United States Patent
Yamada et al.

(10) Patent No.: US 10,290,482 B1
(45) Date of Patent: May 14, 2019

(54) TANDEM COLLISION/REACTION CELL FOR INDUCTIVELY COUPLED PLASMA-MASS SPECTROMETRY (ICP-MS)

(71) Applicant: Agilent Technologies, Inc., Santa Clara, CA (US)

(72) Inventors: Noriyuki Yamada, Tokyo (JP); Erina Shimizu, Tokyo (JP); Yu Okamoto, Tokyo (JP)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 15/920,081

(22) Filed: Mar. 13, 2018

(51) Int. Cl.
| | |
|---|---|
| *H01J 49/00* | (2006.01) |
| *H01J 49/10* | (2006.01) |
| *H01J 49/24* | (2006.01) |
| *H01J 49/06* | (2006.01) |
| *H01J 49/28* | (2006.01) |

(52) U.S. Cl.
CPC .......... *H01J 49/005* (2013.01); *H01J 49/063* (2013.01); *H01J 49/067* (2013.01); *H01J 49/105* (2013.01); *H01J 49/24* (2013.01); *H01J 49/282* (2013.01)

(58) Field of Classification Search
USPC ........................................ 250/281, 282, 292
See application file for complete search history.

(56) References Cited

U.S. PATENT DOCUMENTS

| | | | |
|---|---|---|---|
| 5,847,386 A | 12/1998 | Thomson et al. | |
| 6,265,717 B1 | 7/2001 | Sakata et al. | |
| 7,671,329 B2 | 3/2010 | Sakata et al. | |
| 7,872,227 B2 | 1/2011 | Yamada et al. | |
| 8,610,053 B2 | 12/2013 | Yamada et al. | |
| 2007/0084998 A1* | 4/2007 | Franzen | H01J 49/004 250/287 |
| 2011/0284741 A1* | 11/2011 | Stoermer | H01J 49/0072 250/292 |

OTHER PUBLICATIONS

Agilent 8900 Triple Quadrupole ICP-MS. Leave Interferences Behind with MS/MS. 5991-6900EN. Jun. 1, 2016 (twelve (12) pages).
Agilent ICP-MS Journal. 5991-8559EN. Oct. 2017—Issue 70 (eight (8) pages).
Amr, Mohamed A., The collision/reaction cell and its application in inductively coupled plasma mass spectrometry for the determination of radioisotopes: A literature review. Advances in Applied Science Research, 2012, 3 (4):2179-2191 (thirteen (13) pages).
Beaugrand, Claude et al. Ion Confinement in the Collision Cell of a Multiquadrupole Mass Spectrometer: Access to Chemical Equilibrium and Determination of Kinetic and Thermodynamic Parameters of an Ion-Molecule Reaction. Anal. Chem. 1989, 61, p. 1447-1453 (seven (7) pages).

(Continued)

*Primary Examiner* — Kiet T Nguyen

(57) ABSTRACT

A tandem collision/reaction cell for an inductively coupled plasma-mass spectrometry (ICP-MS) system includes a first ion guide, a second ion guide, and an intermediate electrode in the vicinity of an exit end of the first ion guide. A DC potential barrier is applied to the intermediate electrode. The cell may provide two or more stages of an ion-molecule collision process.

20 Claims, 10 Drawing Sheets

(56) References Cited

OTHER PUBLICATIONS

Dolnikowski, G. G. et al. Ion-Trapping Technique for Ion/Molecule Reaction Studies in the Center Quadrupole of a Triple Quadrupole Mass Spectrometer. International Journal of Mass Spectrometry and Ion Processes, 82 (1988) 1-15 (sixteen (16) pages).

Ors and Helium Mode for More Effective Interference Removal in Complex Samples. Agilent 7800 Quadrupole ICP-MS. Agilent flyer. 5990-7574EN. Jun. 1, 2015 (two (2) pages).

Standard Operation Procedure for Trace Element Analysis of Flue Gas Desulfurization Wastewaters Using ICP-MS Collision/Reaction Cell Procedure. US Environmental Protection Agency. Mar. 2013 (thirty-two (32) pages).

Wolf, Ruth E. What is ICP-MS? . . . and more importantly, what can it do? USGS/CR/CICT, Mar. 2005 (seven (7) pages).

\* cited by examiner

US 10,290,482 B1

TANDEM COLLISION/REACTION CELL FOR INDUCTIVELY COUPLED PLASMA-MASS SPECTROMETRY (ICP-MS)

TECHNICAL FIELD

The present invention relates generally to inductively coupled plasma-mass spectrometry (ICP-MS), and particularly to ICP-MS utilizing a collision/reaction cell.

BACKGROUND

Inductively coupled plasma-mass spectrometry (ICP-MS) is often utilized for elemental analysis of a sample, such as to measure the concentration of trace metals in the sample. An ICP-MS system includes a plasma-based ion source to generate plasma to break molecules of the sample down to atoms and then ionize the atoms in preparation for the elemental analysis. In a typical operation, a liquid sample is nebulized, i.e., converted to an aerosol (a fine spray or mist), by a nebulizer (typically of the pneumatic assisted type) and the aerosolized sample is directed into a plasma plume generated by a plasma source. The plasma source often is configured as a flow-through plasma torch having two or more concentric tubes. Typically, a plasma-forming gas such as argon flows through an outer tube of the torch and is energized into a plasma by an appropriate energy source (typically a radio frequency (RF) powered load coil). The aerosolized sample flows through a coaxial central tube (or capillary) of the torch and is emitted into the as-generated plasma. Exposure to plasma breaks the sample molecules down to atoms, or alternatively partially breaks the sample molecules into molecular fragments, and ionizes the atoms or molecular fragments.

The resulting analyte ions, which are typically positively charged, are extracted from the plasma source and directed as an ion beam into a mass analyzer. The mass analyzer applies a time-varying electrical field, or a combination of electrical and magnetic fields, to spectrally resolve ions of differing masses on the basis of their mass-to-charge (m/z) ratios, enabling an ion detector to then count each type of ion of a given m/z ratio arriving at the ion detector from the mass analyzer. Alternatively the mass analyzer may be a time of flight (TOF) analyzer, which measures the times of flight of ions drifting through a flight tube, from which m/z ratios may then be derived. The ICP-MS system then presents the data so acquired as a spectrum of mass (m/z ratio) peaks. The intensity of each peak is indicative of the concentration (abundance) of the corresponding element of the sample.

In addition to analyte ions for which analysis is sought, the plasma produces background (non-analyte) ions. Certain types of non-analyte ions, referred to as interfering ions, can interfere with the analysis of certain types of analytes. The interfering ions may be produced from the plasma-forming gas (e.g., argon), matrix components of the sample, solvents/acids included in the sample, or air (oxygen and nitrogen) entrained into the system. For example, the interfering ions may be isobaric interferents that have the same nominal mass as an analyte ion. The detection of such interfering ions along with the detection of certain analyte ions leads to spectral overlap in the analytical data, thereby reducing the quality of the analysis. Examples of interfering ions include polyatomic ions such as argon oxide, $^{40}Ar^{16}O^+$, which interferes with the iron isotope $^{56}Fe^+$ because both ions appear at m/z=56 in mass spectra, and argon $^{40}Ar^+$, which interferes with the calcium isotope $^{40}Ca^+$ because both ions appear at m/z=40.

Known approaches for addressing the problem of spectral interference and improving the performance of an ICP-MS system have involved improvements in matrix separation, the use of cool plasma technology, and the use of mathematical correction equations in the processing of the analytical data. These approaches have known limitations. To further address the problem, it is also known to provide a collision/reaction cell in the ICP-MS system between the ion source and the mass analyzer. The cell includes an ion guide that focuses the ion beam along the central axis of the cell. The cell is filled with either a collision gas or a reactive gas. The use of a collision gas (e.g., helium, He) relies on kinetic energy discrimination (KED) by which polyatomic ion interference can be suppressed. Both the analyte ions and the polyatomic interfering ions in the cell undergo multiple collisions with the collision gas molecules, and lose kinetic energy (KE) and thus are decelerated as a result. However, because the polyatomic ions have larger cross-sections than the analyte ions, the polyatomic interfering ions undergo a greater number of collisions and thus lose more kinetic energy than the analyte ions. KED can therefore be utilized to separate the analyte ions from the polyatomic interfering ions, as appreciated by persons skilled in the art.

Theoretically, when carrying out the ion-molecule collision process, the degree of the interference reduction increases with the average number of collisions the ions experience. For example, when $Fe^+$ and $ArO^+$ experience 20 and 40 collisions on average with helium, respectively, the ion intensity ratio $Fe^+/ArO^+$ is higher than when the two ions experience 10 and 20 collisions on average. A higher collision gas (e.g., He) density in the cell (flow rate) is therefore preferable. But this is only true as long as the analyte ions (e.g., $Fe^+$) maintain sufficient post-collision KE to surmount the DC potential barrier. In other words, the collision/reaction cell performance is limited by the upper limit of collision gas density (flow rate), which corresponds to the thermalization (and consequently stalling) of the analyte ions.

Therefore, there is a need for an improved collision/reaction cell and method for performing ion-molecule collisions to address the problem of interferences.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a tandem collision/reaction cell includes: a housing comprising a cell entrance, a cell exit spaced from the cell entrance along a longitudinal axis of the collision/reaction cell, and a gas supply port communicating with an interior of the housing; a first ion guide positioned in the housing and comprising a first ion guide entrance and a first ion guide exit, the first ion guide configured to generate a first RF confining field effective to confine ions in a radial direction orthogonal to the longitudinal axis; a second ion guide positioned in the housing and comprising a second ion guide entrance and a second ion guide exit, the second ion guide configured to generate a second RF confining field effective to confine ions in a radial direction orthogonal to the longitudinal axis; and an intermediate electrode configured to generate an on-axis DC potential barrier in a vicinity of the first ion guide exit, wherein the on-axis DC potential barrier is effective to prevent at least some interfering ions from exiting the first ion guide and low enough to allow analyte ions of smaller cross-section than the interfering ions to exit the first ion guide.

According to another embodiment, an inductively coupled plasma-mass spectrometry (ICP-MS) system includes: a tandem collision/reaction cell according to any of the embodiments disclosed herein; and a mass analyzer communicating with the cell exit.

According to another embodiment, a method for operating a tandem collision/reaction cell in an inductively coupled plasma-mass spectrometry (ICP-MS) system includes: flowing a collision/reaction gas into the tandem collision/reaction cell, the tandem collision/reaction cell comprising a cell entrance, a cell exit spaced from the cell entrance along a longitudinal axis of the tandem collision/reaction cell, a first ion guide between the cell entrance and a second ion guide, and the second ion guide between the first ion guide and the cell exit; generating a first RF confining field in the first ion guide and a second RF confining field in the second ion guide, the first RF electrical field and the second RF electrical field configured to confine ions in a radial direction orthogonal to the longitudinal axis; generating a first DC potential barrier in a vicinity of a first ion guide exit of the first ion guide; generating a second DC potential barrier downstream from a second ion guide exit end of the second ion guide; transmitting analyte ions and interfering ions through the cell entrance and into the first ion guide, the analyte ions and the interfering ions having been produced from ionizing a sample under analysis, wherein the analyte ions and the interfering ions collide with the collision/reaction gas and lose kinetic energy, and the first DC potential barrier is high enough to prevent at least some of the interfering ions from exiting the first ion guide and low enough to allow the analyte ions to exit the first ion guide; and transmitting the analyte ions from the first ion guide into the second ion guide, wherein the analyte ions and any interfering ions in the second ion guide collide with the collision/reaction gas and lose kinetic energy, and the second DC potential barrier is high enough to prevent at least some of the interfering ions from reaching or passing through a mass analyzer downstream from the cell exit, and low enough to allow the analyte ions to the analyte ions be transmitted through the mass analyzer.

According to another embodiment, a method for analyzing a sample includes: producing analyte ions from the sample; transmitting the analyte ions into a tandem collision/reaction cell according to any of the embodiments disclosed herein; operating the tandem collision/reaction cell according to any of the embodiments disclosed herein; and transmitting the analyte ions into a mass analyzer.

According to another embodiment, an inductively coupled plasma-mass spectrometry (ICP-MS) system includes: an ion source configured to generate plasma and produce analyte ions in the plasma; a tandem collision/reaction cell according to any of the embodiments disclosed herein; and a controller comprising an electronic processor and a memory, and configured to control the steps of generating the first RF field, generating the second RF field, generating the first DC potential barrier, and generating the second DC potential barrier according to any of the embodiments disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Figure 1:
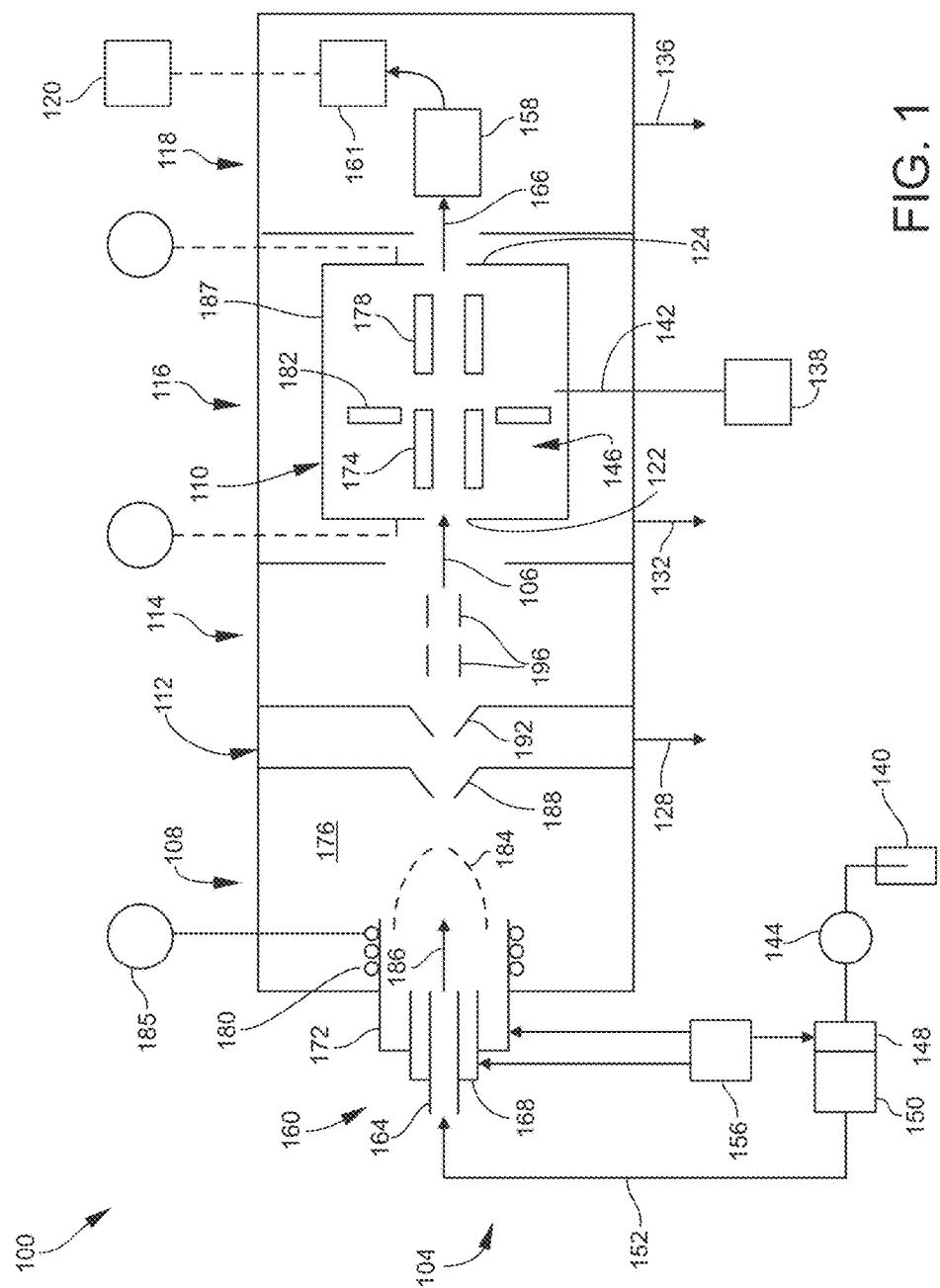
FIG. 1 is a schematic view of an example of an inductively coupled plasma-mass spectrometry (ICP-MS) system according to an embodiment of the present disclosure.

As used herein, the term "fluid" is used in a general sense to refer to any material that is flowable through a conduit. Thus, the term "fluid" may generally refer to either a liquid or a gas, unless specified otherwise or the context dictates otherwise.

As used herein, the term "liquid" may generally refer to a solution, a suspension, or an emulsion. Solid particles and/or gas bubbles may be present in the liquid.

As used herein, the term "aerosol" generally refers to an assembly of liquid droplets and/or solid particles suspended in a gaseous medium long enough to be observed and measured. The size of aerosol droplets or particles is typically on the order of micrometers (μm). See Kulkarni et al., Aerosol Measurement, 3rd ed., John Wiley & Sons, Inc. (2011), p. 821. An aerosol may thus be considered as comprising liquid droplets and/or solid particles and a gas that entrains or carries the liquid droplets and/or solid particles.

As used herein, the term "atomization" refers to the process of breaking molecules down to atoms. Atomization may be carried out, for example, in a plasma enhanced environment. In the case of a liquid sample, "atomizing" may entail nebulizing the liquid sample to form an aerosol, followed by exposing the aerosol to plasma or to heat from the plasma.

As used herein, a "liquid sample" includes one or more different types of analytes of interest dissolved or otherwise carried in a liquid matrix. The liquid matrix includes matrix components. Examples of "matrix components" include, but are not limited to, water and/or other solvents, acids, soluble materials such as salts and/or dissolved solids, undissolved solids or particulates, and any other compounds that are not of analytical interest.

For convenience in the present disclosure, unless specified otherwise or the context dictates otherwise, a "collision/reaction cell" refers to a collision cell, a reaction cell, or a collision/reaction cell configured to operate as both a collision cell and a reaction cell, such as by being switchable between a collision mode and a reaction mode.

For convenience in the present disclosure, unless specified otherwise or the context dictates otherwise, a "collision/reaction gas" refers to an inert collision gas utilized to collide with ions in a collision/reaction cell without reacting with such ions, or a reactive gas utilized to react with analyte ions or interfering ions in a collision/reaction cell.

As used herein, the term "analyte ion" generally refers to any ion produced by ionizing a component of a sample being analyzed by an inductively coupled plasma-mass spectrometry (ICP-MS) system, for which mass spectral data is sought. In the specific context of ICP-MS, analyte ions are typically positive monatomic ions of a metal or other element except for a rare (noble) gas (e.g., argon), or are product ions produced by reacting a collision/reaction gas with positive monatomic ions of a metal or other element except for a rare gas.

As used herein, the term "interfering ion" generally refers to any ion present in a collision/reaction cell that interferes with an analyte ion. Examples of interfering ions include, but are not limited to, positive plasma (e.g., argon) ions, polyatomic ions containing plasma-forming gases (e.g., argon), and polyatomic ions containing a component of the sample. The component of the sample may be an analyte element or a non-analyte species such as may be derived from the matrix components of the sample or other background species.

FIG. 1 is a schematic view of an example of an inductively coupled plasma-mass spectrometry (ICP-MS) system 100 according to an embodiment. Generally, the structures and operations of various components of ICP-MS systems are known to persons skilled in the art, and accordingly are described only briefly herein as necessary for understanding the subject matter being disclosed.

In the present illustrative embodiment, the ICP-MS system 100 generally includes a sample introduction section 104, an ion source 108, an interface section 112, an ion optics section 114, an ion guide section 116, a mass analysis section 118, and a system controller 120. The ICP-MS system 100 also includes a vacuum system configured to exhaust various internal regions of the system 100. The vacuum system maintains desired internal pressures or vacuum levels in the internal regions, and in doing so removes neutral molecules not of analytical interest from the ICP-MS system 100. The vacuum system includes appropriate pumps and passages communicating with ports of the regions to be evacuated, as depicted by arrows 128, 132, and 136 in FIG. 1.

The sample introduction section 104 may include a sample source 140 for providing the sample to be analyzed, a pump 144, a nebulizer 148 for converting the sample into an aerosol, a spray chamber 150 for removing larger droplets from the aerosolized sample, and a sample supply conduit 152 for supplying the sample to the ion source 108, which may include a suitable sample injector. The nebulizer 148 may, for example, utilize a flow of argon or other inert gas (nebulizing gas) from a gas source 156 (e.g., a pressurized reservoir) to aerosolize the sample, as depicted by a downward arrow. The nebulizing gas may be the same gas as the plasma-forming gas utilized to create plasma in the ion source 108, or may be a different gas. The pump 144 (e.g., peristaltic pump, syringe pump, etc.) is connected between the sample source 140 and the nebulizer 148 to establish a flow of liquid sample to the nebulizer 148. The sample flow rate may be in the range between, for example, 0.1 and a few milliliters per minute (mL/min). The sample source 140 may, for example, include one or more vials. A plurality of vials may contain one or more samples, various standard solutions, a tuning liquid, a calibration liquid, a rinse liquid, etc. The sample source 140 may include an automated device configured to switch between different vials, thereby enabling the selection of a particular vial for present use in the ICP-MS system 100.

In another embodiment, the sample may be a gas and not require a nebulizer 148. In another embodiment, the sample source 140 may be or include a pressurized reservoir containing a liquid or gas sample and not require the pump 144. In another embodiment, the sample source 140 may be the output of an analytical separation instrument such as, for example, a liquid chromatography (LC) or gas chromatography (GC) instrument. Other types of devices and means for sample introduction into ICP-MS systems are known and need not be described herein.

The ion source 108 includes a plasma source for atomizing and ionizing the sample. In the illustrated embodiment, the plasma source is flow-through plasma torch such as an ICP torch 160. The ICP torch 160 includes a central or sample injector 164 and one or more outer tubes concentrically arranged about the sample injector 164. In the illustrated embodiment, the ICP torch 160 includes an intermediate tube 168 and an outermost tube 172. The sample injector 164, intermediate tube 168, and outermost tube 172 may be constructed from, for example, quartz, borosilicate glass, or a ceramic. The sample injector 164 alternatively may be constructed from a metal such as, for example, platinum. The ICP torch 160 is located in an ionization chamber (or "torch box") 176. A work coil 180 (also termed a load coil or RF coil) is coupled to a radio frequency (RF) power source 185 and is positioned at the discharge end of the ICP torch 160.

In operation, the gas source 156 supplies a plasma-forming gas to the outermost tube 172. The plasma-forming gas is typically, but not necessarily, argon. RF power is applied to the work coil 180 by the RF power source 185 while the plasma-forming gas flows through the annular channel formed between the intermediate tube 168 and the outermost tube 172, thereby generating a high-frequency, high-energy electromagnetic field to which the plasma-forming gas is exposed. The work coil 180 is operated at a frequency and power effective for generating and maintaining plasma from the plasma-forming gas. A spark may be utilized to provide seed electrons for initially striking the plasma. Consequently, a plasma plume 184 flows from the discharge end of the ICP torch 160 into a sampling cone 188. An auxiliary gas may be flowed through the annular channel formed between the sample injector 164 and the intermediate tube 168 to keep the upstream end of the discharge 184 away from the ends of the sample injector 164 and the intermediate tube 168. The auxiliary gas may be the same gas as the plasma-forming gas or a different gas. The conduction of gas(es) into the intermediate tube 168 and the outermost tube 172 is depicted in FIG. 1 by arrows directed upward from the gas source 156. The sample flows through the sample injector 164 and is emitted from the sample injector 164 and injected into the active plasma 184, as depicted by an arrow 186. As the sample flows through the heating zones of the ICP torch 160 and eventually interacts with the plasma 184, the sample undergoes drying, vaporization, atomization, and ionization, whereby analyte ions are produced from components (particularly atoms) of the sample, according to principles appreciated by persons skilled in the art.

The interface section 112 provides the first stage of pressure reduction between the ion source 108, which typically operates at or around atmospheric pressure (760 Torr), and the evacuated regions of the ICP-MS system 100. For example, the interface section 112 may be maintained at an operating vacuum of for example around 1-2 Torr by a mechanical roughing pump (e.g., a rotary pump, scroll pump, etc.), while the mass analyzer 120 may be maintained at an operating vacuum of for example around $10^{-6}$ Torr by a high-vacuum pump (e.g., a turbomolecular pump, etc.). The interface section 112 includes a sampling cone 188 positioned across the ionization chamber 176 from the discharge end of the ICP torch 160, and a skimmer cone 192 positioned at a small axial distance from the sampling cone 188. The sampling cone 188 and the skimmer cone 192 have small orifices at the center of their conical structures that are aligned with each other and with the central axis of the ICP torch 160. The sampling cone 188 and the skimmer cone 192 assist in extracting the plasma 184 from the torch into the vacuum chamber, and also serve as gas conductance barriers to limit the amount of gas that enters the interface section 112 from the ion source 108. The sampling cone 188 and the skimmer cone 192 may be metal (or at least the tips defining their apertures may be metal) and may be electrically grounded. Neutral gas molecules and particulates entering the interface section 112 may be exhausted from the ICP-MS system 100 via the vacuum port 128.

The ion optics section 114 may be provided between the skimmer cone 192 and the ion guide section 116. The ion optics section 114 includes a lens assembly 196, which may include a series of (typically electrostatic) ion lenses that assist in extracting the ions from the interface section 112, focusing the ions as an ion beam 106, and accelerating the ions into the ion guide section 116. The ion optics section 114 may be maintained at an operating pressure of for example around $10^{-3}$ Torr by a suitable pump (e.g., a turbomolecular pump). While not specifically shown in FIG. 1, the lens assembly 196 may be configured such that the ion optical axis through the lens assembly 196 is offset (in the radial direction orthogonal to the longitudinal axis) from the ion optical axis through the ion guide section 116, with the ion beam 106 steered through the offset. Such configuration facilitates the removal of neutral species and photons from the ion path.

According to an aspect of the present disclosure, the ion guide section 116 includes a tandem collision/reaction cell (or cell assembly) 110. The tandem collision/reaction cell 110 includes an ion guide assembly 146 positioned in a cell housing 187 axially between a cell entrance and a cell exit. In the present embodiment, the cell entrance and cell exit are provided by ion optics components. Namely, a cell entrance lens 122 is positioned at the cell entrance, and a cell exit lens 124 is positioned at the cell exit. The ion guide assembly 146 has a tandem configuration in that it includes a first ion guide 174 and a second ion guide 178. The first ion guide 174 and the second ion guide 178 each have a linear multipole (e.g., quadrupole, hexapole, or octopole) configuration that includes a plurality of (e.g., four, six, or eight) rod electrodes arranged (typically) in parallel with each other along a common central longitudinal axis of the ion guides 174 and 178. The rod electrodes are each positioned at a radial distance from the longitudinal axis, and are circumferentially spaced from each other about the longitudinal axis. For simplicity, only two such rod electrodes are illustrated in FIG. 1 in the case of either the first ion guide 174 or the second ion guide 178. An RF power source (described further below) applies RF potentials to the rod electrodes of the first ion guide 174 and the second ion guide 178 in a known manner that generates a two-dimensional first RF electric field between the rod electrodes of the first ion guide 174 and a two-dimensional second RF electric field between the rod electrodes of the second ion guide 178. These RF fields serve to focus the ion beam along the longitudinal axis by limiting the excursions of the ions in radial directions relative to the longitudinal axis. In a typical embodiment, the first ion guide 174 and the second ion guide 178 are RF-only devices without the capability of mass filtering. In another embodiment, the first ion guide 174 and/or the second ion guide 178 may function as mass filters, by superposing DC potentials on the RF potentials as appreciated by persons skilled in the art. The ion guide assembly 146 further includes an intermediate electrode 182 positioned in the vicinity of the exit end of the first ion guide 174, which is described further below.

A collision/reaction gas source 138 (e.g., a pressurized reservoir) is configured to flow one or more (e.g., a mixture of) collision/reaction gases into the interior of the tandem collision/reaction cell 110 via a collision/reaction gas feed conduit and port 142 leading into the interior of the cell housing 187. The gas flow rate is on the order of milliliters per minute (mL/min) or milligrams per minute (mg/min). The gas flow rate determines the pressure inside the tandem collision/reaction cell 110. The cell operating pressure may be, for example, in a range from 0.001 Torr to 0.1 Torr. Examples of collision/reaction gases include, but are not limited to, helium, neon, argon, hydrogen, oxygen, water, ammonia, methane, fluoromethane ($CH_3F$), and nitrous oxide ($N_2O$), as well as combinations (mixtures) or two or more of the foregoing. Inert (nonreactive) gases such as helium, neon, and argon are utilized as collision gases. The operation of the tandem collision/reaction cell 110 according to the present disclosure is described in more detail below.

The mass analysis section 118 (also referred to herein as the mass spectrometer) includes a mass analyzer 158 and an ion detector 161. The mass analyzer 158 may be any type suitable for ICP-MS. Examples of mass analyzers include, but are not limited to, multipole electrode structures (e.g., quadrupole mass filters, linear ion traps, three-dimensional Paul traps, etc.), time-of-flight (TOF) analyzers, magnetic and/or electric sector instruments, electrostatic traps (e.g. Kingdon, Knight and ORBITRAP® traps) and ion cyclotron resonance (ICR) traps (FT-ICR or FTMS, also known as Penning traps). The ion detector 161 may be any device configured for collecting and measuring the flux (or current) of mass-discriminated ions outputted from the mass analyzer 158. Examples of ion detectors include, but are not limited to, electron multipliers, photomultipliers, micro-channel plate (MCP) detectors, image current detectors, and Faraday cups. For convenience of illustration in FIG. 1, the ion detector 161 (at least the front portion that receives the ions) is shown to be oriented at a ninety degree angle to the ion exit of the mass analyzer 158. In other embodiments, however, the ion detector 161 may be on-axis with the ion exit of the mass analyzer 158.

In operation, the mass analyzer 158 receives an ion beam 166 from the tandem collision/reaction cell 110 and separates or sorts the ions on the basis of their differing mass-to-charge (m/z) ratios. The separated ions pass through the mass analyzer 158 and arrive at the ion detector 161. The ion detector 161 detects and counts each ion and outputs an electronic detector signal (ion measurement signal) to the data acquisition component of the system controller 120. The mass discrimination carried out by the mass analyzer 158 enables the ion detector 161 to detect and count ions having a specific m/z ratio separately from ions having other m/z ratios (derived from different analyte elements of the sample), and thereby produce ion measurement signals for each ion mass (and hence each analyte element) being analyzed. Ions with different m/z ratios may be detected and counted in sequence. The system controller 120 processes the signals received from the ion detector 161 and generates a mass spectrum, which shows the relative signal intensities (abundances) of each ion detected. The signal intensity so measured at a given m/z ratio (and therefore a given analyte element) is directly proportional to the concentration of that element in the sample processed by the ICP-MS system 100. In this manner, the existence of chemical elements contained in the sample being analyzed can be confirmed and the concentrations of the chemical elements can be determined.

While not specifically shown in FIG. 1, the ion optical axis through the ion guide 146 and cell exit lens 124 may be offset from the ion optical axis through the entrance into the mass analyzer 158, and ion optics may be provided to steer the ion beam 166 through the offset. By this configuration, additional neutral species are removed from the ion path.

The system controller (or controller, or computing device) 120 may include one or more modules configured for controlling, monitoring and/or timing various functional aspects of the ICP-MS system 100 such as, for example, controlling the operations of the sample introduction section 104, the ion source 108, the ion optics section 114, the ion guide section 116, and the mass analysis section 118, as well as controlling the vacuum system and various gas flow rates, temperature and pressure conditions, and any other sample processing components provided between the illustrated devices. The system controller 120 is representative of the electrical circuitry (e.g., RF and DC voltage sources) utilized to operate the tandem collision/reaction cell 110. The system controller 120 may also be configured for receiving the detection signals from the ion detector 161 and performing other tasks relating to data acquisition and signal analysis as necessary to generate data (e.g., a mass spectrum) characterizing the sample under analysis. The system controller 120 may include a non-transitory computer-readable medium that includes non-transitory instructions for performing any of the methods disclosed herein. The system controller 120 may include one or more types of hardware, firmware and/or software, as well as one or more memories and databases, as needed for operating the various components of the ICP-MS system 100. The system controller 120 typically includes a main electronic processor providing overall control, and may include one or more electronic processors configured for dedicated control operations or specific signal processing tasks. The system controller 120 may also include one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., non-transitory logic instructions embodied in software, data, and the like). The system controller 120 may include an operating system (e.g., Microsoft Windows® software) for controlling and managing various functions of the system controller 120.

It will be understood that FIG. 1 is a high-level schematic depiction of the ICP-MS system 100 disclosed herein. As appreciated by persons skilled in the art, other components such as additional structures, devices, and electronics may be included as needed for practical implementations, depending on how the ICP-MS system 100 is configured for a given application.

Figure 2:
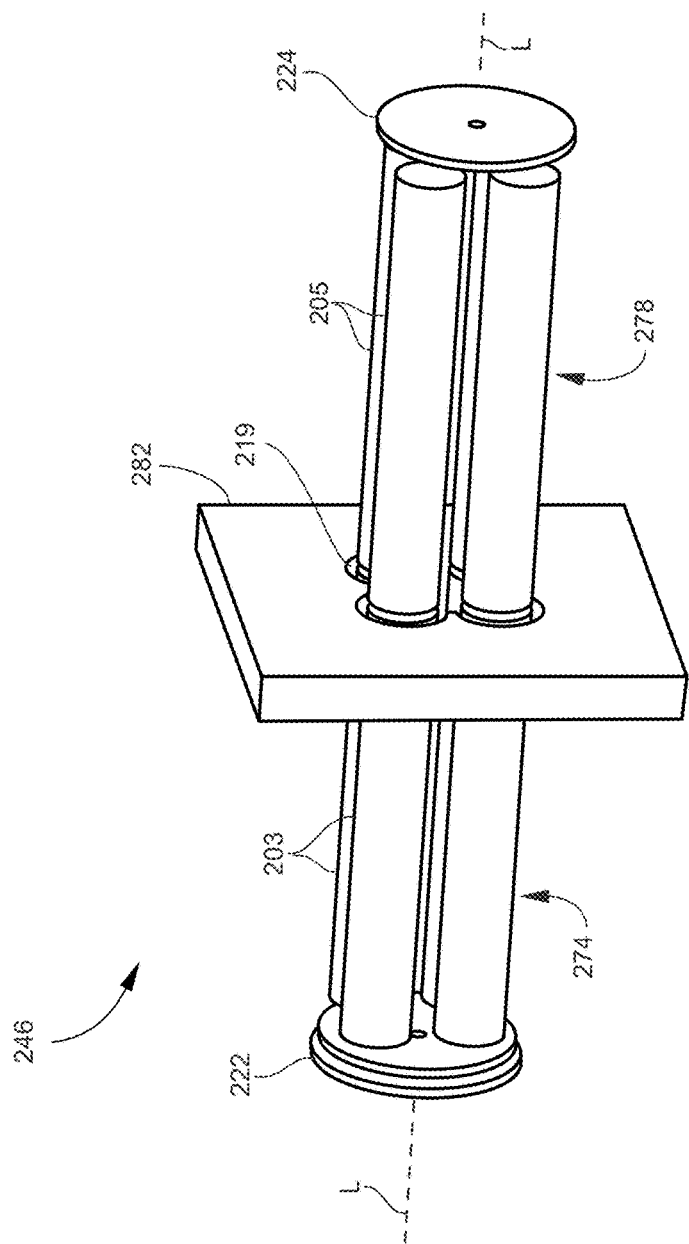
FIG. 2 is a schematic perspective view of an example of a tandem ion guide assembly for a collision/reaction cell according to an embodiment of the present disclosure.
Figure 3A:
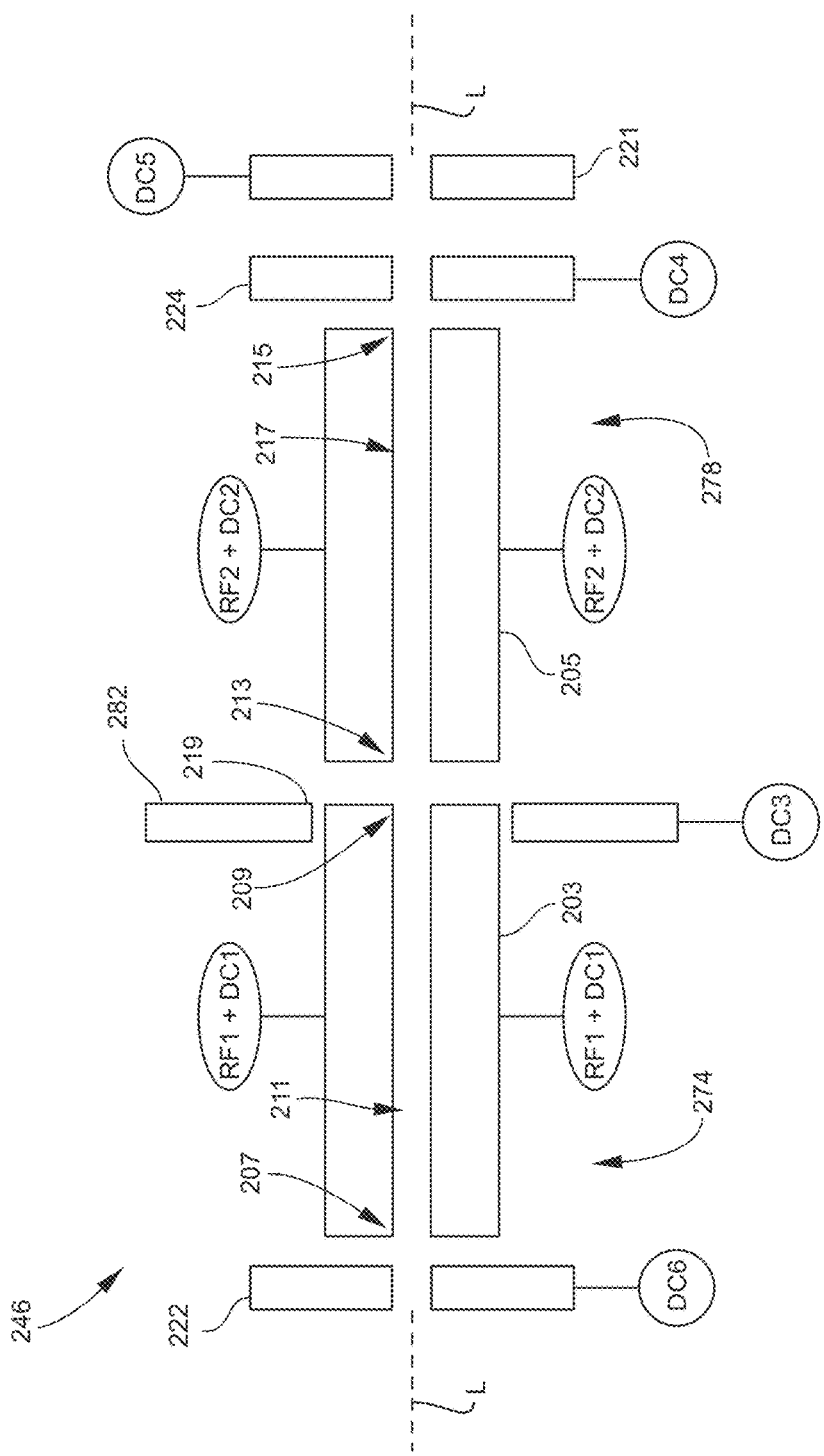
FIG. 3A is a schematic side (lengthwise) view of the tandem ion guide assembly illustrated in FIG. 2.

FIG. 2 is a schematic perspective view of an example of a tandem ion guide assembly 246 according to an embodiment. FIG. 3A is a schematic side (lengthwise) view of the tandem ion guide assembly 246. The tandem ion guide assembly 246 is configured for operation in a collision/reaction cell assembly such as the tandem collision/reaction cell assembly 110 described herein and illustrated in FIG. 1. The tandem ion guide assembly 246 includes a first ion guide 274 and a second ion guide 278 positioned between the cell entrance and the cell exit. A cell entrance lens 222 may be positioned at the cell entrance, and a cell exit lens 224 may be positioned at the cell exit.

The first ion guide 274 includes a plurality of first ion guide electrodes 203 (or "rod electrodes"), and the second ion guide 278 includes a plurality of second ion guide electrodes 205 (or "rod electrodes"). The first ion guide electrodes 203 are circumferentially spaced from each other about a longitudinal axis L of the tandem ion guide assembly 246. Each first ion guide electrode 203 is positioned at a radial distance from (and orthogonal to) the longitudinal axis L and is elongated along the longitudinal axis L. Accordingly, the first ion guide electrodes 203 define a first ion guide entrance 207 near the cell entrance lens 222, a first ion guide exit 209 axially spaced from the first ion guide entrance 207 by an axial length of the first ion guide electrodes 203, and an axially elongated first ion guide interior 211 extending from the first ion guide entrance 207 to the first ion guide exit 209. Likewise, the second ion guide electrodes 205 are circumferentially spaced from each other about the longitudinal axis L (typically the same axis as the first ion guide 274), positioned at a radial distance from (and orthogonal to) the longitudinal axis L, and elongated along the longitudinal axis L. The second ion guide electrodes 205 define a second ion guide entrance 213 axially spaced from the first ion guide exit 209 by a small axial gap, a second ion guide exit 215 axially spaced from the second ion guide entrance 213 by an axial length of the second ion guide electrodes 205 and near the cell exit lens 224, and an axially elongated second ion guide interior 217 extending from the second ion guide entrance 213 to the second ion guide exit 215.

FIG. 2 illustrates one embodiment in which the first ion guide 274 and the second ion guide 278 each have a quadrupole configuration (four ion guide electrodes). In other embodiments, the first ion guide 274 and second ion guide 278 may have a higher-order multipole configuration, for example a hexapole (six ion guide electrodes), octopole (eight ion guide electrodes), or even higher-order multipole configuration. As shown in FIG. 2, the first ion guide electrodes 203 and the second ion guide electrodes 205 may be cylindrical with circular cross-sections. Alternatively, in the quadrupole case the surface of the first ion guide electrodes 203 and the second ion guide electrodes 205 facing the first ion guide interior 211 and second ion guide interior 217, respectively, may have a hyperbolic profile. As another alternative the first ion guide electrodes 203 and the second ion guide electrodes 205 may have polygonal (prismatic) cross-sections.

The tandem ion guide assembly 246 further includes an intermediate electrode 282 configured to generate a DC potential barrier on the axis in the vicinity of the first ion guide exit 209. In one embodiment, the intermediate electrode 282 surrounds the first ion guide 274 at the first ion guide exit 209. In this case, the intermediate electrode 282 has an aperture 219 in which the exit ends of the first ion guide electrodes 203 are disposed. The inside surface of the intermediate electrode 282 defining the aperture 219 is spaced from the outer surfaces of the first ion guide electrodes 203. However, the inside surface of the aperture 219 partly protrudes between the first ion guide electrodes 203 so as to generate a DC potential barrier in the first ion guide interior 211 when a potential higher than the first ion guide potential is applied to the intermediate electrode 282. FIG. 2 illustrates one non-exclusive example in which the aperture 219 includes four protrusions between the four first ion guide electrodes 203. The intermediate electrode 282 does not necessarily have an aperture 219. Wedge-shaped electrodes inserted between the first ion guide electrodes 203 can serve the purpose of generating a potential barrier.

FIG. 3A further schematically illustrates electronics (electrical circuitry) that may be utilized to apply RF and DC potentials to various components of the tandem ion guide assembly 246. The system controller 120 described above and illustrated in FIG. 1 may be considered as being representative of such electronics. In FIG. 3A, the electronics are schematically depicted as a first RF source RF1 superimposed on a first DC source DC1 communicating with the first ion guide electrodes 203, a second RF source RF2 superimposed on a second DC source DC2 communicating with the second ion guide electrodes 205, and a third DC source DC3 communicating with the intermediate electrode 282. The electronics may further include one or more of the following: a fourth DC source DC4 communicating with the cell exit lens 224, a fifth DC source DC5 communicating with an external ion optics component 221, and a sixth DC source DC6 communicating with the cell entrance lens 222. The RF and DC sources may also be referred to collectively as a "voltage source" or "voltage sources." The external ion optics component 221 is external to (outside of) the tandem collision/reaction cell assembly 110, i.e., downstream from the cell exit lens 224. For example, the external ion optics component 221 may be an ion lens positioned between the collision/reaction cell assembly 110 and a mass analyzer or at the entrance of the mass analyzer, or may be multipole electrodes of the mass analyzer itself.

In operation, the first RF source applies RF potentials, RF1, superimposed on DC bias potentials, DC1, to the first ion guide electrodes 203 (RF1+DC1) at a frequency and amplitude effective to generate a two-dimensional, time-varying first RF field in the first ion guide 274. Typically, each opposing pair of first ion guide electrodes 203 is electrically interconnected. The RF potential applied to one opposing pair of first ion guide electrodes 203 is 180 degrees out of phase with the RF potential applied to an adjacent opposing pair of first ion guide electrodes 203 (−RF1+DC1, not shown in FIG. 3), as appreciated by persons skilled in the art. The RF field radially confines the ions in the first ion guide 274, i.e., limits the motions of the ions in the radial direction, thereby focusing the ions as an ion beam concentrated on the longitudinal axis L. The second RF source applies RF potentials, RF2, superimposed on DC bias potentials, DC2, to the second ion guide electrodes 205 in the same manner, thereby generating a two-dimensional, time-varying second RF field in the second ion guide 278 that radially confines the ions in the second ion guide 278 and consequently focuses the ions as an ion beam concentrated on the longitudinal axis L. In this manner, the first ion guide 274 and the second ion guide 278 are operated as RF-only ion guides in which the RF fields function only to focus the ions along the longitudinal axis L.

In another embodiment, however, in which the first ion guide 274 and/or the second ion guide 278 has a quadrupole electrode structure, DC fields with opposite polarities, ±U1 and/or ±U2, may be superposed on the first RF fields and/or the second RF fields to enable the first ion guide 274 and/or the second ion guide 278 to function as a mass filter. Namely, +RF1+U1+DC1 may be applied to one pair of the first ion guide electrodes 203; −RF1−U1+DC1 may be applied to the other pair of the first ion guide electrodes 203; +RF2+U2+DC2 may be applied to one pair of the second ion guide electrodes 205; −RF2−U2+DC2 may be applied to the other pair of the second ion guide electrodes 205. According to known principles, by appropriately selecting the operating parameters of the composite RF/DC field (RF amplitude, RF frequency, and DC magnitude), the first ion guide 274 and/or the second ion guide 278 can be configured to impose a mass range (bandpass) that allows only a single ion mass, or a narrow range of ion masses (from a low-mass cut-off point to a high-mass cut-off point), to pass through the first ion guide 274 and/or the second ion guide 278. Ions having masses within the mass bandpass have stable trajectories and are able to traverse the entire length of the first ion guide 274 and/or the second ion guide 278. Ions having masses outside the mass bandpass have unstable trajectories and thus will be rejected. That is, such ions will overcome the RF confining field and be removed from the first ion guide 274 and/or the second ion guide 278 without the possibility of exiting the first ion guide 274 and/or the second ion guide 278. The mass bandpass can be adjusted by adjusting one or more of the operating parameters of the composite RF/DC field, enabling the selection of a specific ion mass or masses to be transmitted out from the first ion guide 274 and/or the second ion guide 278 at any given time. In some embodiments, this "scanning" function may be implemented to facilitate the process of suppressing the contribution of interfering ions to the mass spectral data, as described elsewhere herein.

The various DC sources are utilized to apply DC bias voltages, at desired magnitudes and polarities, to the components to which they are coupled. In an embodiment, the first DC source DC1 applies a negative DC bias potential to the first ion guide electrodes 203 that is constant along their length, and the second DC source DC2 applies a negative DC bias potential to the second ion guide electrodes 205 that is constant along their length.

As non-exclusive examples, the voltage source(s) is configured to apply potentials having magnitudes in one or more of the following ranges: the first DC bias potential is in a range from −50 V to −10 V, the second DC bias potential is in a range from −100 V to −20 V, the third DC potential is in a range from −50 V to +500 V, and the fourth DC potential (in this case, an on-axis potential applied by the fourth DC source DC4 to the cell exit lens 224) is in a range from −90 V to 0 V. The polarity (positive or negative) of the third DC potential may depend on, for example, the magnitude of the first DC bias potential, the shape of the intermediate electrode 282, the design of the collision/reaction cell 110, and/or various operating conditions of the collision/reaction cell 110.

In another embodiment, the first DC source DC1 and/or the second DC source DC2 may be configured to generate an axial DC gradient along the length of the first ion guide electrodes 203 and/or the second ion guide electrodes 205, respectively. For this purpose, the first DC source supplies two different DC potentials, DC1a and DC1b, which may be coupled to the entrance and exit ends of the first ion guide electrodes 203, respectively, and/or the second DC source supplies two different potentials, DC2a and DC2b, which may be coupled to the entrance and exit ends of the second ion guide electrodes 205, respectively. For example, the DC potentials DC1a and DC1b may be coupled to electrically conductive or resistive layers of the first ion guide electrodes 203 at the entrance and exit ends, and/or the DC potentials DC2a and DC2b may be coupled to electrically conductive or resistive layers of the second ion guide electrodes 205 at the entrance and exit ends. Application of an axial DC potential gradient may be useful to keep ions moving in the forward direction and prevent back flow of the ions. Additionally or alternatively, after transmitting ions into the first ion guide 274 for a desired amount of time, the DC potential DC6 applied to the cell entrance lens 222 may be increased to prevent ions in the first ion guide 274 from escaping first ion guide 274 through the cell entrance lens 222 and prevent additional ions from being transferred into the first ion guide 274 from the ion source 108 (FIG. 1).

Figure 3B:
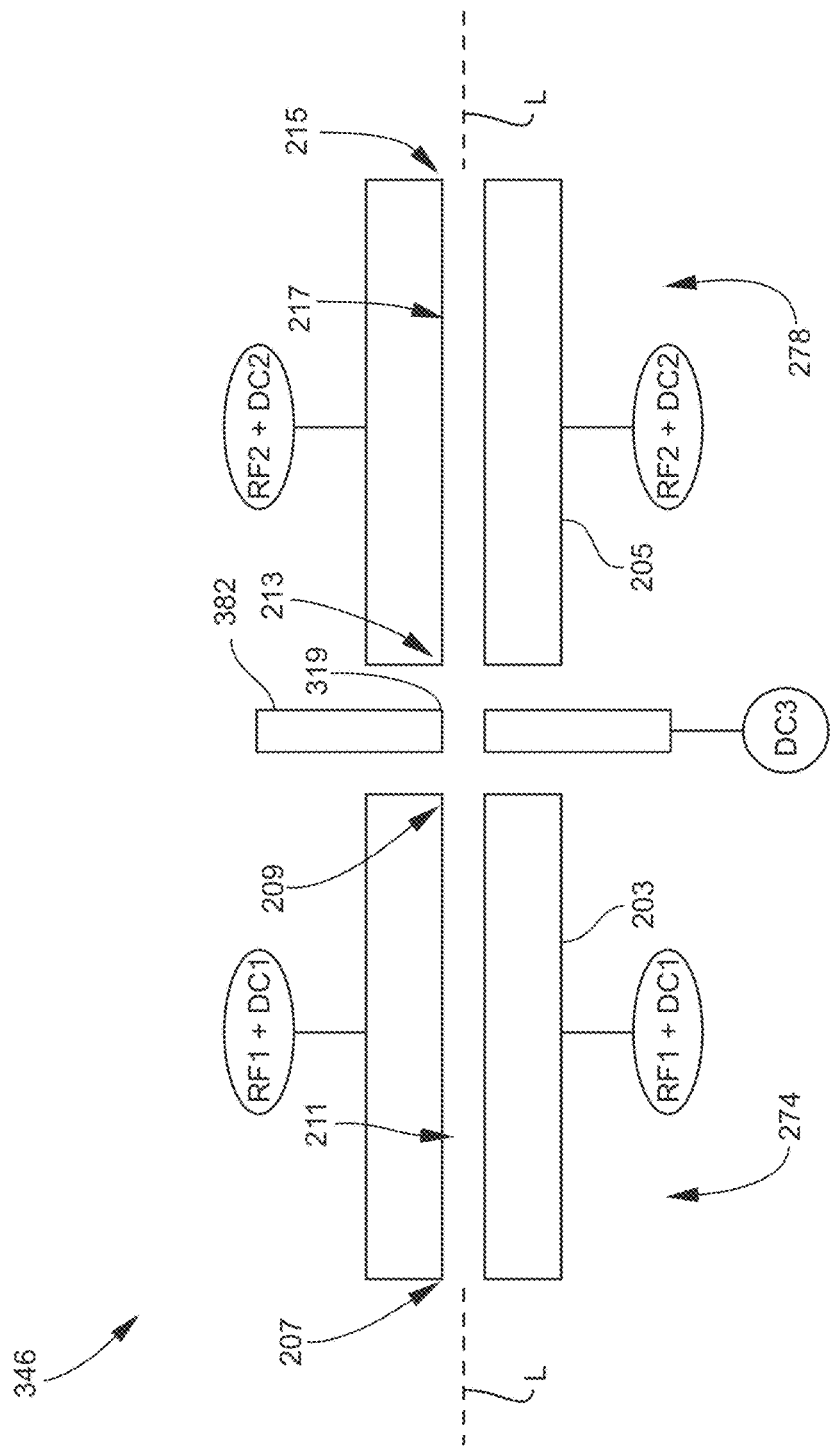
FIG. 3B is a schematic side (lengthwise) view of an example of a tandem ion guide assembly according to another embodiment of the present disclosure.
Figure 3C:
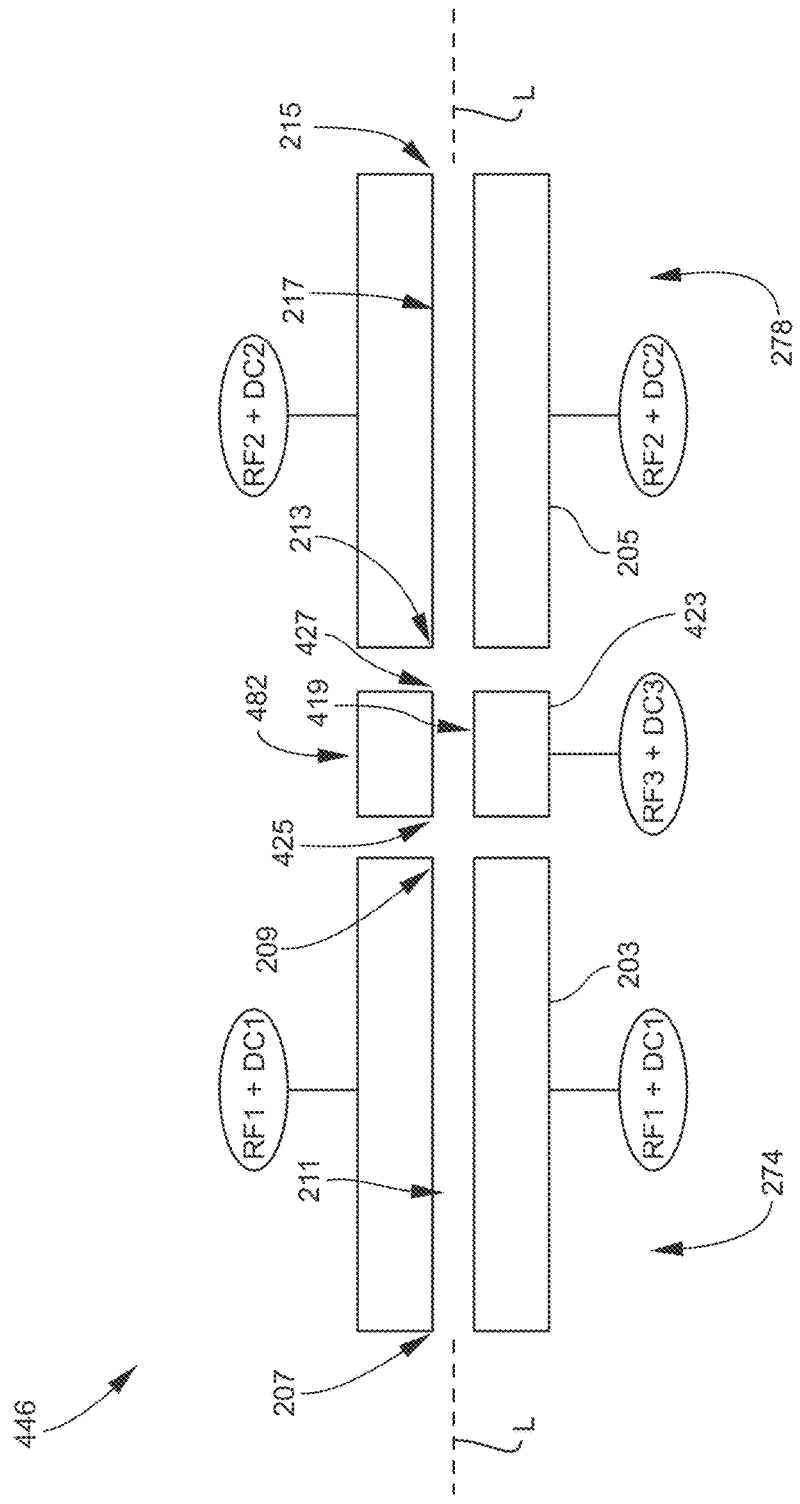
FIG. 3C is a schematic side (lengthwise) view of an example of a tandem ion guide assembly according to another embodiment of the present disclosure.

FIGS. 3B and 3C illustrate other examples of an intermediate electrode positioned in the vicinity of a first ion guide exit 209.

FIG. 3B is a schematic side (lengthwise) view of an example of a tandem ion guide assembly 346 according to another embodiment. The ion guide assembly 346 is similar to the ion guide assembly 246 described above in conjunction with FIG. 3A. The ion guide assembly 346 thus includes a first ion guide 274 and a second ion guide 278 having multipole configurations, and an intermediate electrode 382 having an aperture 319. The ion guide assembly 346 differs in that the intermediate electrode 382 is a plate axially positioned between the first ion guide exit 209 and the second ion guide entrance 213. The third DC source DC3 communicates with the intermediate electrode 382, and applies a DC potential to the intermediate electrode 382 to create an on-axis DC potential barrier as described elsewhere herein.

FIG. 3C is a schematic side (lengthwise) view of an example of a tandem ion guide assembly 446 according to another embodiment. The ion guide assembly 446 is similar to the ion guide assembly 246 described above in conjunction with FIG. 3A. The ion guide assembly 446 thus includes a first ion guide 274 and a second ion guide 278 having multipole configurations, and an intermediate electrode. The ion guide assembly 446 differs in that the intermediate electrode is an intermediate (or third) ion guide 482 axially positioned between the first ion guide exit 209 and the second ion guide entrance 213. The third ion guide 482 has a multipole configuration, which may be of the same order as the first ion guide 274 and the second ion guide 278 (e.g., quadrupole, hexapole, octopole, etc.). The third ion guide 482 thus has a plurality of intermediate (or third) guide electrodes 423 circumferentially spaced from each other about the longitudinal axis L, positioned at a radial distance from the longitudinal axis L, and elongated along the longitudinal axis L. From the side view of FIG. 3C, only two (one opposing pair of) third guide electrodes 423 are shown. The third guide electrodes 423 define a third ion guide entrance 425 axially spaced from the first ion guide exit 209 by a small axial gap, a third ion guide exit 427 axially spaced from the second ion guide entrance 213 by small axial gap, and an axially elongated third ion guide interior 419 extending from the third ion guide entrance 425 to the third ion guide exit 427. The third ion guide 482 is of shorter length than the first ion guide 274 and the second ion guide 278. As one non-exclusive example, the axial length of the third ion guide 482 (i.e., the third guide electrodes 423) may in a range of 10% to 60% of the axial lengths of the first ion guide 274 and the second ion guide 278. In this embodiment, in operation the intermediate electrode (third ion guide 482) is configured to generate a third RF confining field in its interior as well as an on-axis DC potential barrier as described elsewhere herein. For example, the voltage source(s) communicating with the third guide electrodes 423 is configured to apply a third RF potential superimposed on a third DC potential (RF3+DC3) to create the on-axis DC potential barrier and the third RF confining field.

Thus far, the first ion guide 274 and the second ion guide 278 have been described and illustrated primarily as having a linear multipole configuration in which the first ion guide electrodes 203 and the second ion guide electrodes 205 are parallel to each other and to the longitudinal axes of the first ion guide 274 and the second ion guide 278. In other embodiments, however, the first ion guide electrodes 203 and/or the second ion guide electrodes 205 may not be parallel. Instead, the first ion guide electrodes 203 and/or the second ion guide electrodes 205 may converge toward or diverge away from each other and the longitudinal axis, along their length in the direction from the entrance end to the exit end.

In still other embodiments, the first ion guide 274 and/or the second ion guide 278 may not have a linear multipole configuration. More generally, the first ion guide 274 and the second ion guide 278 may have any configuration effective generate a first RF confining field in the first ion guide 274 and a second RF confining field in the second ion guide 278, and which is compatible with the generation of a DC potential barrier in the vicinity of the exit of the first ion guide 274 in accordance with the subject matter disclosed herein. As one non-exclusive alternative embodiment, the first ion guide electrodes 203 and/or the second ion guide electrodes 205 may be a series (or stack) of rings (or plates with apertures) coaxially surrounding the longitudinal axis and axially spaced from each about the longitudinal axis. In this case, to generate an RF confining field in the first ion guide 274 and/or the second ion guide 278, the RF potential applied to a given ring or plate may be 180 degrees out of phase with the RF potential applied to the ring(s) or plate(s) that are immediately adjacent to that given ring or plate. The inside diameters of the apertures of the rings or plates may be constant along the longitudinal axis. Alternatively, the inside diameters of the apertures of the rings or plates may successively increase or decrease at successive rings or plates in the direction from the entrance to the exit, such as in the manner of an ion funnel. The structure and operation of axially stacked rings or plates, and ion funnels, for use as ion guides are generally known to persons skilled in the art.

Figure 4:
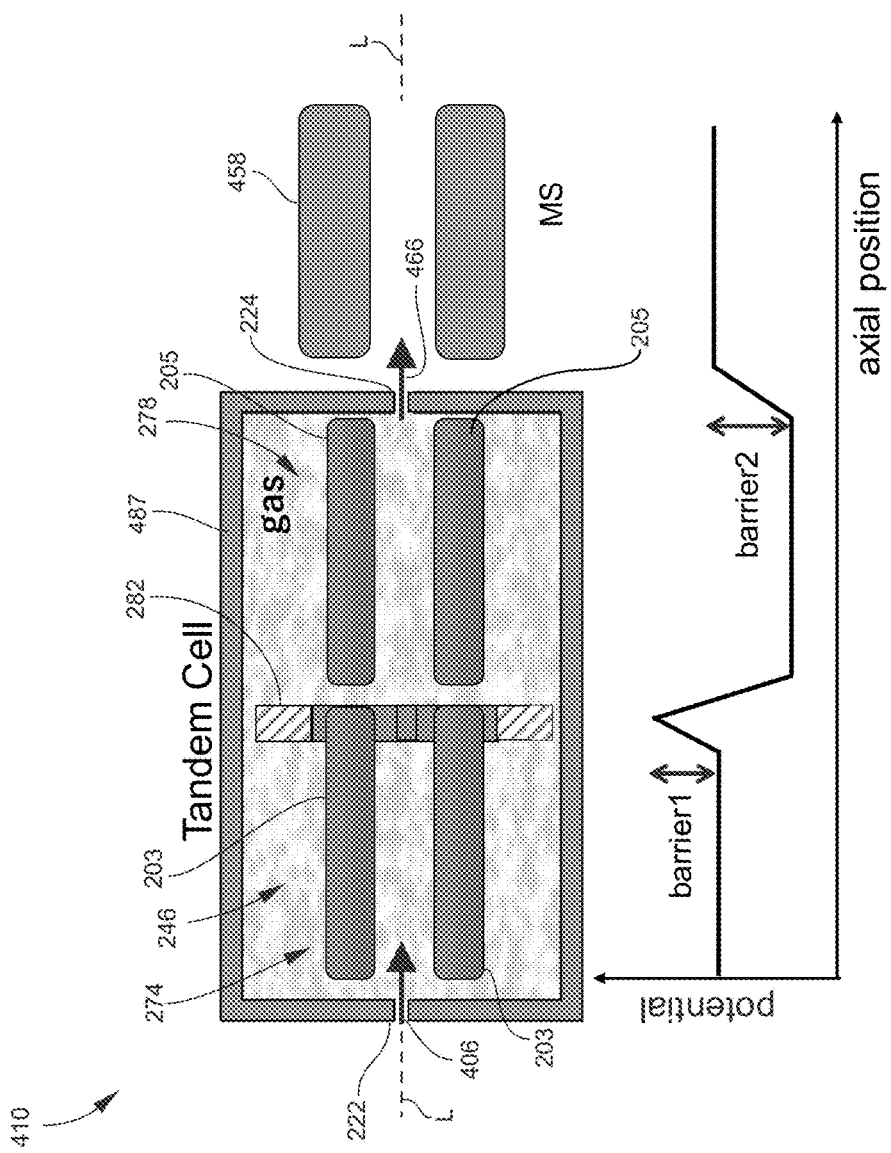
FIG. 4 is a schematic side (lengthwise) view of an example of a tandem collision/reaction cell assembly, and a plot of direct current (DC) potential as a function of axial position, according to an embodiment of the present disclosure.

FIG. 4 is a schematic side (lengthwise) view of an example of a tandem collision/reaction cell (or cell assembly) 410. The tandem collision/reaction cell 410 includes a housing 487 in which the tandem ion guide assembly 246 is operatively mounted. FIG. 4 also illustrates a mass analyzer 458. By example, the mass analyzer 458 is depicted as a quadrupole device (only one pair of opposing rod electrodes being shown), but may be any type of mass analyzer as described herein. FIG. 4 further includes a plot of direct current (DC) potential generated on axis as a function of axial position along the length of the tandem collision/reaction cell 410 and mass analyzer 458.

In the operation of an ICP-MS system, ideally only the analyte ions produced in the plasma-based ion source would be transmitted to the mass analyzer 458. However, as noted earlier in the present disclosure, the ion source 108 (FIG. 1) also produces background (non-analyte) ions, or "interfering ions," which may interfere with the analysis of a given sample. The interfering ions may be produced from the plasma-forming gas (e.g., argon), matrix components of the sample, solvents/acids included in the sample, and air (oxygen and nitrogen) entrained into the system. As noted earlier in the present disclosure, an example of interfering ions are polyatomic interferents that have the same nominal mass as a monatomic analyte ion. The detection of such an interfering ion along with the detection of a certain analyte ion (that the interfering ion interferes with) leads to spectral overlap in the analytical data, thereby reducing the quality of the analysis.

The tandem collision/reaction cell 410 (or 110) described herein is configured to remove (reduce or eliminate) interfering ions (mainly polyatomic interferents), thereby preventing the interfering ions from being transmitted (or at least reducing the amount of interfering ions transmitted) into the mass analyzer 458. Consequently, the operation of the tandem collision/reaction cell 410 improves the performance of the ICP-MS system and the quality of the mass spectral data produced thereby. The tandem collision/reaction cell 410 may accomplish this by implementing a multi-stage ion-molecule collision process.

The operation of the collision/reaction cell 410 will be described with reference primarily being made to FIGS. 3 and 4. A flow of collision/reaction gas (e.g., helium) is established into the collision/reaction cell 410 via the collision/reaction gas source 138 and feed port 142 (FIG. 1). The gas flow rate is set to be optimized for the specific element (analyte ion) being measured. The gas flow rate may depend on other factors such as, for example, the type of plasma-generating gas being utilized (typically argon) and the type(s) of interfering ion(s) anticipated to be removed. The first ion guide 274 and the second ion guide 278 are actively powered by the RF sources RF1 and RF2 to generate respective first and second RF ion confining fields as described above. The first DC source DC1 applies a negative first DC bias potential (or guide potential) to the first ion guide electrodes 203, and the second DC source DC2 applies a negative second DC bias potential (or guide potential) to the second ion guide electrodes 205. The magnitude of the second DC bias potential is more negative than the first DC bias potential. As one non-exclusive example, the first DC bias potential may be −22 V and the second DC bias potential may be −65 V. The third DC source DC3 applies a DC potential to the intermediate electrode 282 with a magnitude effective to generate a first DC potential barrier on the longitudinal axis L (i.e., an on-axis DC potential barrier). As such, the third DC source DC3 applies a DC potential that is more positive than the first DC bias potential. As shown in FIG. 4, the first DC potential barrier (or barrier height) may be defined as the difference between the on-axis potential generated at the end of the first ion guide by the DC potential applied to the intermediate electrode 282 and the first DC bias potential applied to the first ion guide electrodes 203. A second DC potential barrier on the longitudinal axis L is generated at an axial position downstream from the second ion guide 278. As examples, the second potential barrier may be generated by applying a DC potential at the entrance of the mass analyzer 458, or an ion optics component 221 (FIG. 3A) located between the collision/reaction cell 410 and the mass analyzer 458. As shown in FIG. 4, the second DC potential barrier (or barrier height) may be defined as the difference between the DC potential applied to the entrance of the mass analyzer 458 and the second DC bias potential applied to the second ion guide electrodes 205.

As non-exclusive examples, the magnitude of the first DC potential barrier is in a range from 0.1 V to 10 V, and/or the magnitude of the second DC potential barrier is in a range from 0.1 V to 10 V.

While the collision/reaction gas is flowing into the collision/reaction cell 410 and the RF and DC fields are generated, an ion beam 406 is transmitted into the first ion guide 274 via the cell entrance lens 222. The ion beam 406 includes both analyte ions and background (non-analyte) ions. Depending on the sample under analysis and the operating conditions of the sample introduction section 104 and ion source 108 (FIG. 1), some of the non-analyte ions in the ion beam 406 may be interfering ions. For example, the background ions may or may not function as interfering ions for the particular type of analyte ion being measured. The incoming ions are accelerated into the first ion guide 274 to a kinetic energy of, for example, about 22 eV. The ions are radially confined as a beam along the longitudinal axis L by the first RF field in the first ion guide 274. After entering the tandem collision/reaction cell 410 and being focused by the first RF field, the ions are subjected to multiple collisions with the molecules of the collision/reaction gas and are thereby decelerated. According to the principle of kinetic energy discrimination (KED), the cross-sections of polyatomic interfering ions (e.g., molecular ions) are larger than monatomic analyte ions of the same mass as the interfering ions. Therefore, the interfering ions experience a greater number of collisions with the collision/reaction gas and thus lose more kinetic energy (KE) as compared with the analyte ions. The magnitude of the first DC potential barrier is high enough to prevent (at least some of) the lower post-collision KE interfering ions from passing from the first ion guide 274 to the second ion guide 278, but is low enough to allow the higher-energy analyte ions to pass from the first ion guide 274 to the second ion guide 278. In this manner, the contribution of interfering ions to the mass spectral data is suppressed.

As the second ion guide 278 is at a lower DC bias than the first ion guide 274, the analyte ions (or at least a majority thereof) are transmitted (re-accelerated) from the first ion guide 274 into the second ion guide 278. Any interfering ions that are able to overcome the first DC potential barrier generated at the intermediate electrode 282 also pass into the second ion guide 278. The analyte ions and interfering ions are radially confined as a beam along the longitudinal axis L by the second RF field in the second ion guide 278, and undergo additional collisions with the collision/reaction gas molecules in the second ion guide 278. Again, the interfering ions experience a greater number of collisions with the collision/reaction gas and thus lose more kinetic energy as compared with the analyte ions. The magnitude of the second DC potential barrier is high enough to prevent (at least some of) the interfering ions from reaching or passing through the mass analyzer 458, but is low enough to allow the analyte ions to be transmitted as an ion beam 466 into the mass analyzer 458 and reach the detector. Ideally, this outgoing ion beam 466 should have no (or at least a much lower concentration of) interfering ions than the incoming ion beam 406. In this manner, the interfering ions are prevented from entering the mass analyzer 458, and thus do not contribute to the ion measurement signal and do not cause spectral overlap with the analyte ions, thereby further suppressing the interference. The ion-molecule collision process is able to remove multiple types of interfering polyatomic ions that interfere with multiple types of analytes.

Notably, the re-acceleration of the analyte ions in the second ion guide 278 enables the flow rate of the collision/reaction gas to be higher than is conventional. The increased gas flow rate corresponds to an increased density of the collision/reaction gas in the collision/reaction cell 410. Consequently, the increased gas flow rate increases the average number of collisions the ions experience, therefore increasing the effectiveness of the collision/reaction cell 410 in suppressing interferences. The re-acceleration of the analyte ions in the second ion guide 278 allows the analyte ions to surmount the second DC potential barrier even in the presence of the higher-density collision/reaction gas. Accordingly, a tandem collision/reaction cell as disclosed herein increases the upper limit of collision gas density (flow rate). By comparison, in a conventional cell such analyte ions would stall and not be able to reach the mass analyzer. As one non-exclusive example in the case of helium, the gas flow rate into the tandem collision/reaction cell 410 may be 12 mL/min. By comparison, the gas flow rate into a conventional collision/reaction cell may be 5 mL/min Comparative Example The performance of a tandem collision/reaction cell as described herein was compared to the performance of a standard (conventional) collision/reaction cell, namely a cell containing only a single multipole ion guide. In each case, a multi-element solution with a 2% hydrochloric acid (HCl) was run through the ICP-MS system. Table 1 below shows the experimental conditions of the standard cell and the tandem cell. Table 2 below shows the signal-to-background (S/B) ratios for four analytes interfered with, demonstrating that the tandem cell performed significantly better than the standard cell (i.e., improved reduction of polyatomic interferences). Table 3 shows the signal intensity for the same four analytes, again demonstrating that the tandem cell performed significantly better than the standard cell.

TABLE 1

| | Measurement conditions | | | | |
|---|---|---|---|---|---|
| | He flow rate (mL/min) | First bias (V) | Barrier1 Height (V) | Second bias (V) | Barrier2 Height (V) |
| Standard cell | 5 | −18 | 0 | −18 | 3 |
| Tandem cell | 12 | −22 | 2 | −65 | 4 |

TABLE 2

Experimental results: S/B ratio for interfered elements
S/B ratio

| | $V^+/ClO^+$ | $Fe^+/ArO^+$ | $As^+/ArCl^+$ | $Se^+/Ar_2^+$ |
|---|---|---|---|---|
| Standard cell | 3.4 | 4.2 | 43 | 10 |
| Tandem cell | 21 | 7.2 | 210 | 88 |

TABLE 3

Experimental results: Signal intensity of interfered elements
Ion signal intensity per unit concentration (counts/s/ppb)

| | V | Fe | As | Se |
|---|---|---|---|---|
| Standard cell | 21760 | 35320 | 5690 | 464 |
| Tandem cell | 22030 | 44470 | 6760 | 618 |

Operating Principles of Tandem Cell Versus Conventional Cell

The operating principles of a tandem collision/reaction cell as disclosed herein in comparison to a conventional collision/reaction cell is further described below.

1. Ion Kinetic Energies of the Analyte Ion and Interfering Ion

Consider two ion species A (atomic analyte ions) and B (polyatomic ions that interfere with A). The B ions have the same mass, or m/z ratio, as the A ions, but are larger than the A ions. It is assumed that the B ions collide with gas molecules twice more frequently than the A ions due to their larger size (larger collision cross-section). At the entrance of the collision cell, the A and B ions have the same initial kinetic energy, Ei, which is given by the instrument operating conditions. The initial kinetic energy Ei is typically around 20 eV. In the collision cell, both the A and B ions both slow down step by step each time they collide with collision gas molecules. In the hard-sphere collision model, the final kinetic energy, the kinetic energy that an ion has at the exit of the collision cell, is approximately given by:

$$E_f = E_i \left\{ \frac{m_i^2 + m_g^2}{(m_i + m_g)^2} \right\}^N \quad (1)$$

where $m_i$ and $m_g$ are the masses of the ion and gas molecule, respectively, and N is the number of collisions that the ion experiences in the collision cell. Because N is larger for the B ions than for the A ions on average, $E_f$ is smaller for the B ions than for the A ions, as calculated from Eq. (1). For example, the approximate final energies, $Ef_A$ and $Ef_B$, are calculated from Eq. (1) for $A={}^{51}V^+$ ions ($m_i$=51u)

colliding 10 times and B=$^{35}$Cl$^{16}$O$^+$ ions (m$_i$=51u) colliding 20 times with He gas (m$_g$=4u), respectively, as:

Ef$_A$=0.235Ei, and

Ef$_B$=0.055Ei, when E$_i$=20 eV, Ef$_A$=4.7 eV, and Ef$_B$=1.1 eV.

Therefore, by setting up a potential barrier of 3 eV in height, for example, after the collision cell (post-cell barrier, barrier 2 in FIG. 4), the low-energy B ions are blocked by the barrier while the higher-energy A ions are able to surmount the barrier. In this way, the analyte ions A are selectively detected while the interfering ions B are removed from the ion beam after the potential barrier, even though the mass analyzer is not able to resolve A and B. The technique is known as kinetic energy discrimination (KED) as described elsewhere herein.

2. Overlap of Ion Kinetic Energy Distributions after the Standard Cell

However, N varies from ion to ion even among the same ion species because the collision process is statistical. Therefore, A ions and B ions have their own distributions of number of collisions. The probability of an ion colliding N times is given by the Poisson distribution:

$$P(N) = \frac{N_{ave}^N}{N!}\exp(-N_{ave}) \quad (2)$$

where N$_{ave}$ is the average number of collisions that the ions undergo in the collision cell, which is given by the cell length divided by the mean free path.

Figure 5:
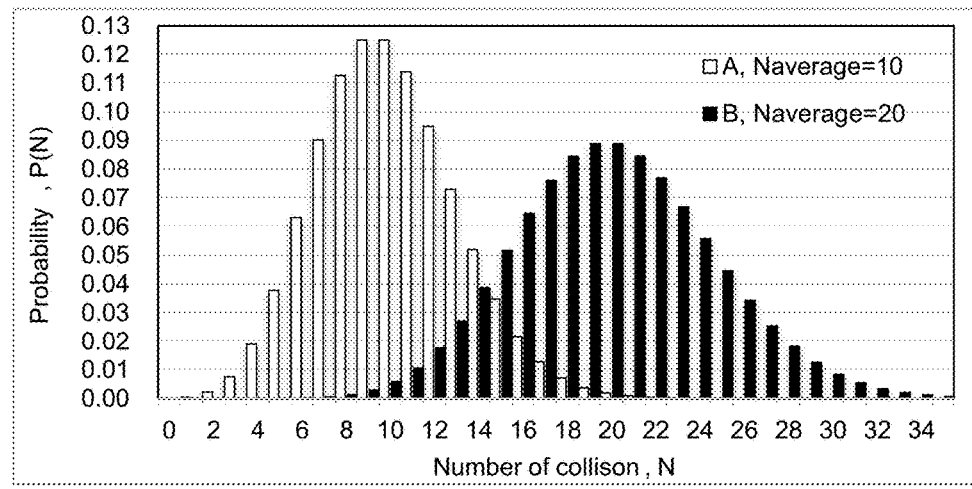
FIG. 5 is a plot of probability distributions of number of collisions between collision gas molecules and analyte ions and interfering ions in a collision/reaction cell, when the analyte ions experience an average of 10 collisions and the interfering ions experience an average of 20 collisions.

For example, when the average numbers of collisions for A and B are N$_{ave}$=10 and 20, respectively, the probability distributions of number of collisions for A and B are shown in FIG. 5. The overlap of the two distributions corresponds to the overlap of the final kinetic energy distributions of A and B. The smaller the overlap, the more efficient is the implementation of KED.

Figure 6:
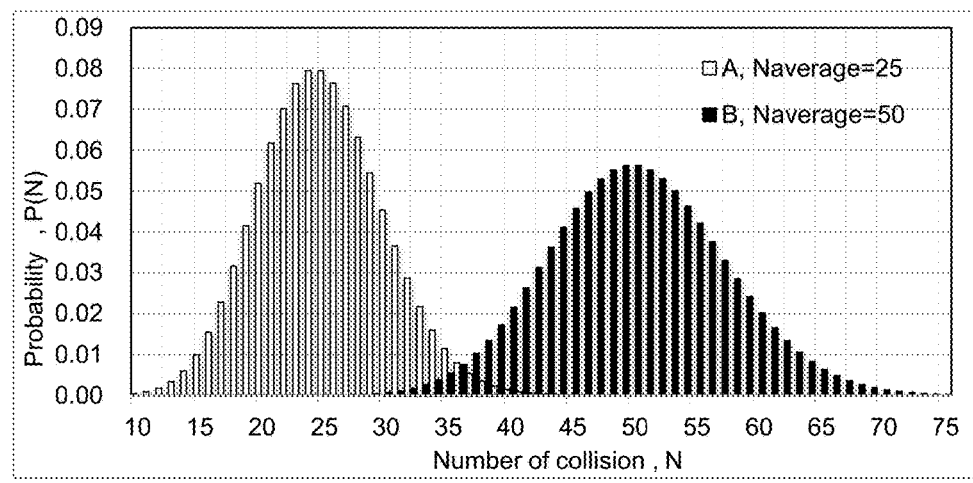
FIG. 6 is a plot of probability distributions of number of collisions between collision gas molecules and analyte ions and interfering ions in a collision/reaction cell, when the analyte ions experience an average of 25 collisions and the interfering ions experience an average of 50 collisions.

If the average numbers of collisions for A and B are increased, the overlap of the collision number distributions decreases according to the characteristics of the Poisson distribution. FIG. 6 shows the distributions of A and B when N$_{ave}$=25 and 50, respectively (the increase of collisions can be easily achieved by increasing the flow rate of the collision gas or extending the cell length). Compared with FIG. 5, the overlap is smaller. More efficient KED, and hence improved performance of the collision cell, will be achieved by increasing a number of collisions or collision gas flow rate.

3. Ion Kinetic Energy Difference

The smaller overlap of the collision number distributions will result in a smaller overlap of the final kinetic energy distributions. But this is only true when the A ions maintain sufficient kinetic energy. In other words, undergoing too many collisions leads to stoppage of ion movement. If the A ions stall as well as the B ions (lose all the initial kinetic energy) before reaching the cell exit, no difference in the final kinetic energy is generated between A and B. Such a situation precludes the implementation of KED. For example, the approximate final energies, Ef$_A$ and Ef$_B$, are calculated from Eq. (1) for A=V$^+$ ions (m$_i$=51u) colliding 25 times and B=ClO$^+$ ions (m$_i$=51u) colliding 50 times with He gas (m$_g$=4u), respectively, as:

Ef$_A$=0.027E$_i$, and

Ef$_B$=0.0007E$_i$, when E$_i$=20 eV, Ef$_A$=0.54 eV (nearly zero) and Ef$_B$=0.01 eV (virtually zero). The energy difference is too small for efficient KED. As the He flow rate (number of collisions) increases, the kinetic energy difference between A and B increases. A further increase in the He flow rate leads to significant loss of kinetic energy for both ions, leading to a reduced difference in kinetic energy. This indicates a limitation of KED for standard collision cells.

4. Enhancement of Ion Kinetic Energy Difference by Lowering the Ion Guide Bias Potential As the final kinetic energy Ef is proportional to the initial kinetic energy Ei, an increase of Ei prevents the stoppage of A ions after increased numbers of collisions and enhances the difference in the final kinetic energy between A and B. The initial kinetic energy Ei can be increased by decreasing the bias potential of the ion guide in the cell, because (positive) ions are accelerated by a lowered potential at the entrance of the cell (ion guide). However, there are two drawbacks to lowering the ion guide bias to a highly negative potential such as −90V: (i) ion transmission in the ion guide has to be compromised; and (ii) ion kinetic energy distribution is broadened toward higher energy, leading to the deterioration of peak shapes in the mass spectrum.

5. Enhancement of Ion Kinetic Energy Difference by Tandem Configuration

These drawbacks are overcome by the tandem configuration where the first part of the ion guide is biased at a standard potential (e.g., −20 V) and the second part is biased more negatively (e.g., −70 V) by which ions are accelerated between the two parts, gaining additional kinetic energy of 70−20=50 eV.

Figure 7:
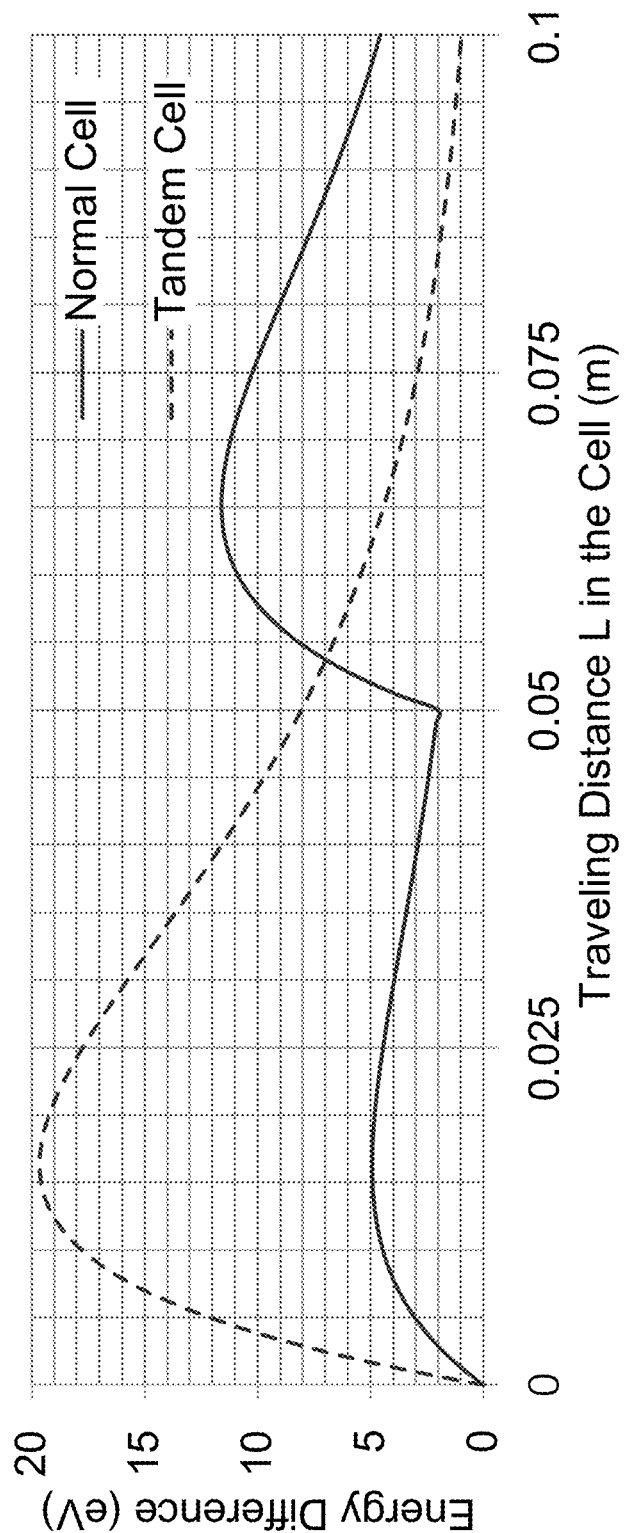
FIG. 7 are plots of the average energy difference between analyte ions and interfering ions inside a conventional collision/reaction cell and a tandem collision/reaction cell described herein.

An example of calculated energy difference using Eq. (1) is shown in FIG. 7, in comparison with a conventional (standard) cell, where the ion's traveling distance L is related with N as N=L/λ (λ is a mean free path for the ion). The energy difference at the cell exit (the cell having a length of L=0.1 m), or the final energy difference, is larger in tandem configuration despite the higher (less negative) bias potential.

6. Overlap of Ion Kinetic Energy Distributions after the Tandem Cell

Although the difference in the average final energy between the A and B ions increases with the tandem configuration, the overlap of the two final energy distributions also increases, which is confirmed by a calculation using Eq, (1) and (2) (not shown). The reason is that in the tandem configuration, even if the two ions experience the same number of collisions, their final energy can be different, depending on where collisions occur in the cell. For example, the kinetic energy of the ion that has experienced seven (7) collisions in the first ion guide and three (3) collisions in the second ion guide can be different from that of the ion that has experienced three (3) collisions in the first and seven (7) collisions in the second, even though the total number of collisions is the same. (It will be noted that, in standard cell, the final kinetic energy does not depend on in which part of the cell an ion undergoes collisions, as a uniform bias potential is established in the cell.) Therefore, efficient KED will not be expected from a tandem cell even if the number of collisions is increased.

7. Addition of Potential Barrier Inside the Tandem Cell (Barrier 1 in FIG. 4)

The problem with the tandem configuration is resolved by the addition of a potential barrier to the end of the first part (in-cell barrier, barrier 1 in FIG. 4). The probability of the interfering B ion's surmounting the post-cell barrier (barrier 2 in FIG. 4) is reduced by barrier 1, thus improving S/B ratio, as explained below.

Suppose that the flow rate of He collision gas into the cell is adjusted so that the average numbers of collisions for A and B are 25 and 50, respectively, and that the first and second ion guides are biased at about −20 V and −70 V, respectively. For the B ions (B1) which undergo 25 collisions in the first part and 25 collisions in the second ion guide, their kinetic energy is (0.53)eV and (1.3)eV at the ends of the first ion guide and the second ion guide (at the cell exit), respectively. Here, $E_i$=20 eV, $m_i$=51u and $m_g$=4u are assumed to calculate according to Eq. (1). Therefore, the post-cell barrier (barrier 2 in FIG. 4) of, for example, 3 eV in height, blocks B1 ions whose kinetic energy is 1.3 eV.

However, there are also B ions that undergo 35 collisions in the first ion guide and 15 collisions in the second ion guide (B2 ions). These B2 ions have kinetic energy of 0.13 eV at the end of the first part and 5.7 eV at the cell exit. Therefore, the post-cell barrier of 3 eV in height cannot block these B2 ions. However, if an in-cell barrier higher than 0.13 eV, (for example 1 eV) is set up, the B2 ions are blocked inside the cell, thus being rejected from the ion beam.

For the analyte ions A, which undergo collisions in half the times of B, the kinetic energy is 3.0 eV and 8.1 eV at the ends of the first and the second ion guide, respectively, when they undergo 13 collisions both in the first and second part (A1 ions). Therefore, these A1 ions overcome both barriers (1 eV height and 3 eV height). Likewise, for the A ions that undergo 18 and 8 collisions at the first and second ion guides (A2 ions), respectively, their kinetic energies are 1.5 eV and 16 eV at the ends of the first and second ion guide, respectively. Thus, the A2 ions overcome both barriers as well.

From these examples, it is evident that the tandem cell with an in-cell barrier provides analyte ions A with sufficient final kinetic energy to be detected even when the number of collisions for the interfering B ions is set to as high as 50.

8. Summary

In summary, to improve collision cell performance, it is necessary to increase a number of collisions (or collision gas density) in the cell. However, the increase of number of collisions brings about large losses in the kinetic energy of analyte ions, which leads to a small difference in kinetic energy between analyte ions and polyatomic interference ions, which in turn precludes efficient KED or improvement of collision cell performance. To maintain a significant difference in the kinetic energy between analyte ions and polyatomic interference ions, a tandem collision cell as described herein is utilized. However, the tandem configuration brings about a larger overlap between the kinetic energy distribution of analyte ions and that of polyatomic interference ions, which degrades KED implementation. With the addition of a potential barrier at the end of the first ion guide of the tandem cell, efficient KED is recovered in the tandem configuration. The tandem cell with an in-cell barrier enables efficient KED under the condition of an increased number of collisions, which improves the collision cell performance (i.e., improves S/B ratios). See N. Yamada, Kinetic energy discrimination in collision/reaction cell ICP-MS: Theoretical review of principles and limitations, *Spectrochimica Acta Part B* 110 (2015) 31-44.

Figure 8:
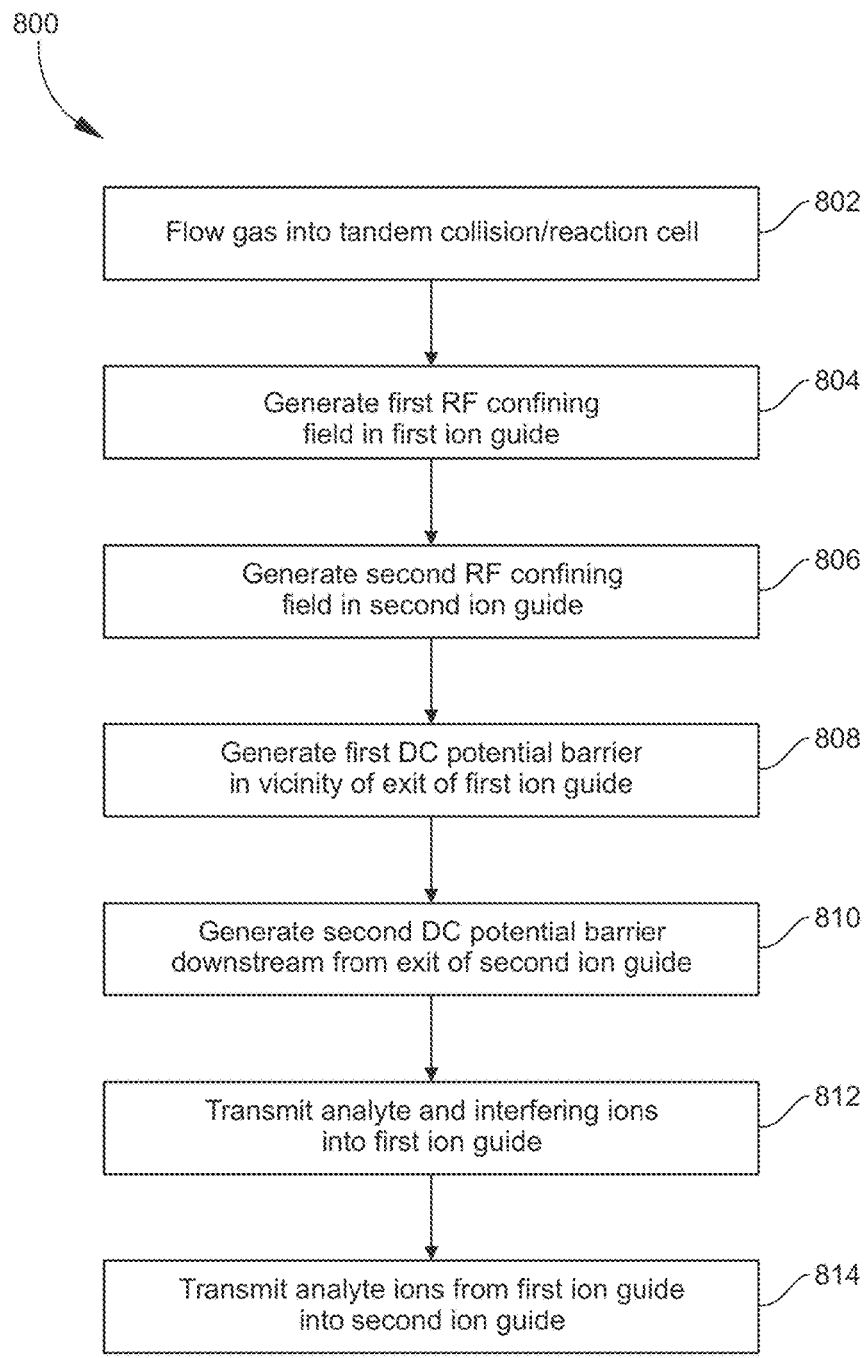
FIG. 8 is a flow diagram illustrating an example of a method for operating a tandem collision/reaction cell in an inductively coupled plasma-mass spectrometry (ICP-MS) system according to an embodiment of the present disclosure.

FIG. 8 is a flow diagram 800 illustrating an example of a method for operating a tandem collision/reaction cell in an inductively coupled plasma-mass spectrometry (ICP-MS) system according to an embodiment. A collision/reaction gas is flowed into the tandem collision/reaction cell (step 802).

The tandem collision/reaction cell includes a cell entrance, a cell exit spaced from the cell entrance along a longitudinal axis of the tandem collision/reaction cell, a first ion guide between the cell entrance and a second ion guide, and the second ion guide between the first ion guide and the cell exit. A first RF confining field is generated in the first ion guide (step 804), and a second RF confining field is generated in the second ion guide (step 806). The first RF electrical field and the second RF electrical field are configured to confine ions in a radial direction orthogonal to the longitudinal axis. A first DC potential barrier is generated in a vicinity of a first ion guide exit of the first ion guide (step 808). A second DC potential barrier is generated at an axial position downstream from the second ion guide exit of the second ion guide (step 810). No specific limitation is placed on the order of the initiation of steps 802-808, and two or more of steps 802-808 may be initiated simultaneously or near simultaneously. Analyte ions and interfering ions, having been produced from ionizing a sample under analysis, are transmitted through the cell entrance and into the first ion guide (step 812). In the first ion guide, the analyte ions and the interfering ions collide with the collision/reaction gas and lose kinetic energy. The first DC potential barrier is set to be high enough to prevent at least some of the interfering ions from exiting the first ion guide, but low enough to allow the analyte ions to exit the first ion guide. The analyte ions are transmitted from the first ion guide into the second ion guide (step 814). Any interfering ions able to surmount the first DC potential barrier also pass into the second ion guide. In the second ion guide, the analyte ions and any interfering ions also present collide with the collision/reaction gas and lose kinetic energy. The second DC potential barrier is set to be high enough to prevent at least some of the interfering ions from reaching or passing through a mass analyzer downstream from the cell exit, but low enough to allow the analyte ions to be transmitted through the mass analyzer. The analyte ions may then be analyzed by the mass analyzer and detected and counted by a downstream ion detector.

In an embodiment, the flow diagram 800 may represent a collision/reaction cell, or a collision/reaction cell and associated electronics, or a collision/reaction cell and associated ICP-MS system configured to carry out steps 802-814. For this purpose, a controller (e.g., the controller 120 shown in FIG. 1) including a processor, memory, and other components as appreciated by persons skilled in the art, may be provided to control the performance of steps 802-814, such as by controlling the components (e.g., the cell, electronics, etc.) of the ICP-MS system involved in carrying out steps 802-814.

Figure 9:
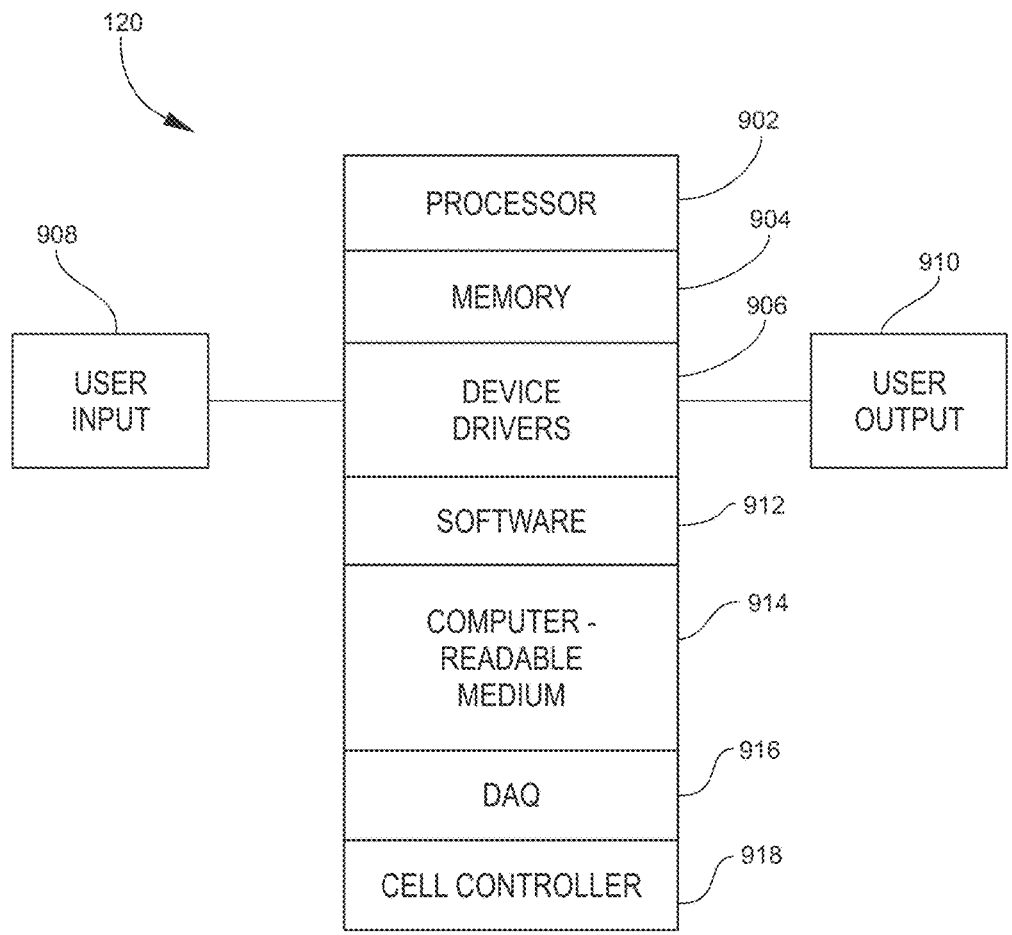
FIG. 9 is a schematic view of a non-limiting example of the system controller (or controller, or computing device) that may be part of or communicate with a spectrometry system such as the ICP-MS system illustrated in FIG. 1.

FIG. 9 is a schematic view of a non-limiting example of the system controller (or controller, or computing device) 120 that may be part of or communicate with a spectrometry system such as the ICP-MS system 100 illustrated in FIG. 1. In the illustrated embodiment, the system controller 120 includes a processor 902 (typically electronics-based), which may be representative of a main electronic processor providing overall control, and one or more electronic processors configured for dedicated control operations or specific signal processing tasks (e.g., a graphics processing unit or GPU, a digital signal processor or DSP, an application-specific integrated circuit or ASIC, a field-programmable gate array or FPGA, etc.). The system controller 120 also includes one or more memories 904 (volatile and/or non-volatile) for storing data and/or software. The system controller 120 may also include one or more device drivers 906 for controlling one or more types of user interface devices and providing an interface between the user interface devices and components of the system controller 120 communicating with the user interface devices. Such user interface devices may include user input devices 908 (e.g., keyboard, keypad, touch screen, mouse, joystick, trackball, and the like) and user output devices 910 (e.g., display screen, printer, visual indicators or alerts, audible indicators or alerts, and the like). In various embodiments, the system controller 120 may be considered as including one or more of the user input devices 908 and/or user output devices 910, or at least as communicating with them. The system controller 120 may also include one or more types of computer programs or software 912 contained in memory and/or on one or more types of computer-readable media 914. The computer programs or software may contain non-transitory instructions (e.g., logic instructions) for controlling or performing various operations of the ICP-MS system 100. The computer programs or software may include application software and system software. System software may include an operating system (e.g., a Microsoft Windows® operating system) for controlling and managing various functions of the system controller 120, including interaction between hardware and application software. In particular, the operating system may provide a graphical user interface (GUI) displayable via a user output device 910, and with which a user may interact with the use of a user input device 908. The system controller 120 may also include one or more data acquisition/signal conditioning components (DAQs) 916 (as may be embodied in hardware, firmware and/or software) for receiving and processing ion measurement signals outputted by the ion detector 161 (FIG. 1), including formatting data for presentation in graphical form by the GUI.

The system controller 120 may further include a cell controller (or control module) 918 configured to control the operation of the collision/reaction cell 110 (or 410) and coordinate and/or synchronize the cell operation with the operations of the ion source 108, the ion optics section 114, the mass analysis section 118, and any other ion processing devices provided in the ICP-MS system 100 illustrated in FIG. 1. Thus, the cell controller 918 may be configured to control or perform all or part of any of the methods disclosed herein, including methods for operating the collision/reaction cell 110. For these purposes, the cell controller 918 may be embodied in software and/or electronics (hardware and/or firmware) as appreciated by persons skilled in the art.

It will be understood that FIG. 9 is high-level schematic depiction of an example of a system controller 120 consistent with the present disclosure. Other components, such as additional structures, devices, electronics, and computer-related or electronic processor-related components may be included as needed for practical implementations. It will also be understood that the system controller 120 is schematically represented in FIG. 9 as functional blocks intended to represent structures (e.g., circuitries, mechanisms, hardware, firmware, software, etc.) that may be provided. The various functional blocks and any signal links between them have been arbitrarily located for purposes of illustration only and are not limiting in any manner Persons skilled in the art will appreciate that, in practice, the functions of the system controller 120 may be implemented in a variety of ways and not necessarily in the exact manner illustrated in FIG. 9 and described by example herein.

Thus far in the present disclosure, the collision/reaction cell 110 (or 410) has been described primarily as a "tandem" cell having two stages. However, the present disclosure encompasses multiple stages beyond two. That is, the collision/reaction cell 110 (or 410) may include more than two distinct ion guides and generate more than two DC potential barriers, such as by including more than two intermediate electrodes.

In an embodiment, in addition to the physical, nonreactive ion-molecule collision process, the collision/reaction cell 110 (or 410) is also capable of implementing a chemically reactive ion-molecule reaction process. Thus, the collision/reaction cell 110 may be configured to operate in (and be switched between) three different operating modes: a collision mode in which a collision gas is flowed into the collision/reaction cell 110, a reaction mode in which a reaction gas is flowed into the collision/reaction cell 110, and a "no-gas" mode in which no type of collision/reaction gas is flowed into the collision/reaction cell 110. The selection of a specific mode may depend on the type of analyte ion(s) being measured and the type of interfering ion(s), if any, to be removed. By "type" is meant the chemical (elemental) identity of the analyte ion (e.g., iron, cadmium, vanadium, etc.) and of the interfering ion (e.g. $ArO^+$, $MoO^+$, $ClO^+$, etc).

Typically, the reaction mode is based on the relative reaction rates of the reactive gas with the analyte ion and the interfering ion. Reactions with interfering ions are exothermic and reactions with analyte ions are endothermic. Hence, reactions with interfering ions are faster than reactions with analyte ions. The reactive gas thus is effectively unreactive with the analyte ions, or may be completely unreactive with the analyte ions. The particular type of reaction that occurs (e.g., charge transfer, proton transfer, etc.) depends on the type of reactive gas utilized and the type of interfering ion to be removed. In one embodiment, the reaction converts the interfering ion to either a non-interfering ion or a neutral species. The conversion of an interfering ion to a non-interfering ion involves changing the composition of the interfering ion, thereby changing the mass of the interfering ion to a mass different from (and thus no longer interfering with) the mass of the analyte ion. In the case of converting an interfering ion to a neutral species, the neutral species is not influenced by electrical or magnetic fields. Thus, the neutral species can be removed by the vacuum system (e.g., via port 132 or port 136) along with other neutral gas molecules, and in any event is "invisible" to the mass analyzer. An example is the use of hydrogen gas $H_2$ to convert the argon ion $^{40}Ar^+$, which interferes with the calcium isotope $^{40}Ca^+$, to the neutral argon atom Ar via charge transfer from the argon ion to the hydrogen molecule: $H_2 + {}^{40}Ar^+ \rightarrow Ar + H_2^+$.

In another embodiment of the reaction mode, the ion-molecule reaction involves the analyte ion instead of the interfering ion. That is, the reaction converts the analyte ion to a new analyte ion species, i.e., changes the composition of the original analyte ion. The new analyte ion species has a mass different from (typically higher than) the mass of the original analyte ion species, and hence also different from the mass of the interfering ion. Reaction with the analyte ion may also be characterized as, in effect, the conversion of the interfered ion to a non-interfered ion. The new analyte ion is detected and becomes part of the mass spectrum, and provides useful information because it corresponds to the original monatomic analyte ion under investigation.

In the no-gas mode, the collision/reaction cell 110 is utilized only as an ion guide to transport analyte ions to the mass analyzer 158. That is, the RF-only ion guide 146 is operated in the absence of a collision/reaction gas. The no-gas mode may be useful when interfering ions are not present such that a collision or reaction operation to suppress interference is not needed.

Exemplary Embodiments

Exemplary embodiments provided in accordance with the presently disclosed subject matter include, but are not limited to, the following:

1. A tandem collision/reaction cell, comprising: a housing comprising a cell entrance, a cell exit spaced from the cell entrance along a longitudinal axis of the collision/reaction cell, and a gas supply port communicating with an interior of the housing; a first ion guide positioned in the housing and comprising a first ion guide entrance and a first ion guide exit, the first ion guide configured to generate a first RF confining field effective to confine ions in a radial direction orthogonal to the longitudinal axis; a second ion guide positioned in the housing and comprising a second ion guide entrance and a second ion guide exit, the second ion guide configured to generate a second RF confining field effective to confine ions in a radial direction orthogonal to the longitudinal axis; and an intermediate electrode configured to generate an on-axis DC potential barrier in a vicinity of the first ion guide exit, wherein the on-axis DC potential barrier is effective to prevent at least some interfering ions from exiting the first ion guide and low enough to allow analyte ions of smaller cross-section than the interfering ions to exit the first ion guide.

2. The tandem collision/reaction cell of claim 1, wherein the on-axis DC potential barrier has a magnitude in a range from 0.1 V to 10 V.

3. The tandem collision/reaction cell of embodiment 1 or 2, wherein the first ion guide and the second ion guide are multipole ion guides.

4. The tandem collision/reaction cell of embodiment 3, wherein: the first ion guide comprises a plurality of elongated first ion guide electrodes positioned at a radial distance orthogonal to the longitudinal axis and circumferentially spaced from each other about the longitudinal axis, and defining the first ion guide entrance and the first ion guide exit; and the second ion guide comprises a plurality of elongated second ion guide electrodes positioned at a radial distance orthogonal to the longitudinal axis and circumferentially spaced from each other about the longitudinal axis, and defining the second ion guide entrance and the second ion guide exit, the second ion guide entrance being spaced from the first ion guide exit by an axial gap.

5. The tandem collision/reaction cell of any of the preceding embodiments, comprising a voltage source configured to apply a first RF potential superimposed on a first DC bias potential to electrodes of the first ion guide to generate the first RF confining field, apply a second RF potential superimposed on a second DC bias potential to electrodes of the second ion guide to generate the second RF confining field, and apply a third DC potential to the intermediate electrode to generate the on-axis DC potential barrier.

6. The tandem collision/reaction cell of embodiment 5, wherein the voltage source has a configuration selected from the group consisting of: the voltage source is configured to apply the first DC bias potential in a range from −50 V to −10 V; the voltage source is configured to apply the second DC bias potential in a range from −100 V to −20 V; the voltage source is configured to apply the third DC potential in a range from −50 V to +500 V; and a combination of two or more of the foregoing.

7. The tandem collision/reaction cell of embodiment 5 or 6, comprising an ion optics component downstream from the second ion guide exit, wherein the voltage source is configured to apply a fourth DC potential to the ion optics component, and the fourth DC potential has a magnitude that produces an on-axis potential more positive than the second DC bias potential.

8. The tandem collision/reaction cell of embodiment 7, wherein the fourth DC potential is in a range from −90 V to 0 V.

9. The tandem collision/reaction cell of any of the preceding embodiments, wherein the intermediate electrode is a plate having an aperture surrounding the first ion guide at the first ion guide exit.

10. The tandem collision/reaction cell of any of embodiments 1-8, wherein the intermediate electrode is a plate comprising an inside surface defining an aperture surrounding the first ion guide at the first ion guide exit, wherein the first ion guide comprises a plurality of first ion guide electrodes arranged in a multipole configuration, and the inside surface protrudes between the first ion guide electrodes.

11. The tandem collision/reaction cell of any of embodiments 1-8, wherein the intermediate electrode is a plate having an aperture between the first ion guide exit and the second ion guide entrance.

12. The tandem collision/reaction cell of any of embodiments 1-8, wherein the intermediate electrode is an ion guide positioned between the first ion guide exit and the second ion guide entrance, and is configured to generate a third RF confining field.

13. The tandem collision/reaction cell of any of embodiments 1-8, wherein the intermediate electrode is a multipole ion guide positioned between the first ion guide exit and the second ion guide entrance, and is configured to generate a third RF confining field.

14. The tandem collision/reaction cell of any of embodiments 1-8, wherein the intermediate electrode, the first ion guide, and the second ion guide are multipole ion guides, the intermediate electrode is positioned between the first ion guide exit and the second ion guide entrance, and the intermediate electrode has a shorter axial length than the first ion guide and the second ion guide.

15. The tandem collision/reaction cell of embodiment 14, wherein the axial length of the intermediate electrode is in a range of 10% to 60% of an axial length of the first ion guide and an axial length of the second ion guide.

16. The tandem collision/reaction cell of any of the preceding embodiments, comprising an ion optics component positioned downstream from the second ion guide exit and configured to generate a second DC potential barrier effective to prevent at least some interfering ions from passing through a mass analyzer downstream from the cell exit, and low enough to allow analyte ions to pass through the mass analyzer.

17. The tandem collision/reaction cell of any of the preceding embodiments, wherein the ion optics component has a position selected from the group consisting of: the ion optics component is positioned at the cell exit; the ion optics component is positioned outside of the housing; the ion optics component is positioned between the cell exit and a mass analyzer; the ion optics component is positioned at an entrance of a mass analyzer; and the ion optics component is a mass analyzer.

18. The tandem collision/reaction cell of any of the preceding embodiments, comprising a collision/reaction gas source configured to flow a collision/reaction gas into the housing via the gas supply port.

19. An inductively coupled plasma-mass spectrometry (ICP-MS) system, comprising: the tandem collision/reaction cell of any of the preceding embodiments; and a mass analyzer communicating with the cell exit.

20. The ICP-MS system of embodiment 19, comprising an ion source communicating with the cell entrance, wherein the ion source comprises a plasma torch.

21. A method for operating a tandem collision/reaction cell in an inductively coupled plasma-mass spectrometry (ICP-MS) system, the method comprising: flowing a collision/reaction gas into the tandem collision/reaction cell, the tandem collision/reaction cell comprising a cell entrance, a cell exit spaced from the cell entrance along a longitudinal axis of the tandem collision/reaction cell, a first ion guide between the cell entrance and a second ion guide, and the second ion guide between the first ion guide and the cell exit; generating a first RF confining field in the first ion guide to confine ions in a radial direction orthogonal to the longitudinal axis; generating a second RF confining field in the second ion guide to confine ions in a radial direction orthogonal to the longitudinal axis; generating a first DC potential barrier in a vicinity of a first ion guide exit of the first ion guide; generating a second DC potential barrier downstream from a second ion guide exit of the second ion guide; transmitting analyte ions and interfering ions through the cell entrance and into the first ion guide, the analyte ions and the interfering ions having been produced from ionizing a sample under analysis, wherein the analyte ions and the interfering ions collide with the collision/reaction gas and lose kinetic energy, and the first DC potential barrier is high enough to prevent at least some of the interfering ions from exiting the first ion guide and low enough to allow the analyte ions to exit the first ion guide; and transmitting the analyte ions from the first ion guide into the second ion guide, wherein the analyte ions and any interfering ions in the second ion guide collide with the collision/reaction gas and lose kinetic energy, and the second DC potential barrier is high enough to prevent at least some of the interfering ions from passing through a mass analyzer downstream from the cell exit, and low enough to allow the analyte ions to pass through the mass analyzer.

22. The method of embodiment 21, wherein the magnitudes of the first DC potential barrier and the second DC potential barrier are selected from the group consisting of: the magnitude of the first DC potential barrier is in a range from 0.1 V to 10 V; the magnitude of the second DC potential barrier is in a range from 0.1 V to 10 V; and both of the foregoing.

23. The method of embodiment 21 or 22, wherein the tandem collision/reaction cell comprises an intermediate electrode in a vicinity of the first ion guide exit, and generating the first DC potential barrier comprises applying a DC potential to the intermediate electrode.

24. The method of any of embodiments 21-23, comprising applying a first RF potential superimposed on a first DC bias potential to the first ion guide to generate the first RF confining field, and a second RF potential superimposed on a second DC bias potential to the second ion guide to generate the second RF confining field.

25. The method of embodiment 24, wherein the first DC bias potential and the second DC bias potential have magnitudes selected from the group consisting of: the first DC bias potential and the second DC bias potential have negative magnitudes; the first DC bias potential is in a range from −50 V to −10 V; the second DC bias potential is in a range from −100 V to −20 V; and the second DC bias potential is more negative than the first DC potential.

26. The method of embodiment 24 or 25, wherein at least one of the first DC bias potential or the second DC bias potential is constant along a length of the first ion guide or the second ion guide.

27. The method of embodiment 24 or 25, wherein at least one of the first DC bias potential or the second DC bias potential is an axial DC potential gradient along a length of the first ion guide or the second ion guide.

28. The method of any of embodiments 21-27, wherein generating the second DC potential barrier comprises applying a DC potential to an ion optics component having a position selected from the group consisting of: the ion optics component is positioned at the cell exit; the ion optics component is positioned outside of the housing; the ion optics component is positioned between the cell exit and a mass analyzer; the ion optics component is positioned at an entrance of a mass analyzer; and the ion optics component is a mass analyzer.

29. The method of any of the preceding embodiments, wherein the collision/reaction gas is helium, neon, or argon.

30. The method of any of the preceding embodiments, wherein the analyte ions comprise positive monatomic ions of a metal or other element except for a rare gas.

31. The method of any of the preceding embodiments, wherein the interfering ions are selected from the group consisting of: polyatomic ions containing argon; and polyatomic ions containing a component of the sample.

32. The method of any of embodiments 21-31, comprising, before transmitting the analyte ions through the entrance and into the collision/reaction cell, producing the analyte ions by exposing the sample to an inductively coupled plasma.

33. The method of embodiment 32, wherein exposing the sample comprises operating a plasma torch.

34. The method of embodiment 33, comprising flowing the sample into the plasma torch from a nebulizer or a spray chamber.

35. A method for analyzing a sample, the method comprising: producing analyte ions from the sample; transmitting the analyte ions into the tandem collision/reaction cell of any of embodiments 21-34; operating the tandem collision/reaction cell according to the method of any of embodiments 21-34; and transmitting the analyte ions into a mass analyzer.

36. An inductively coupled plasma-mass spectrometry (ICP-MS) system, comprising: an ion source configured to generate plasma and produce analyte ions in the plasma; the tandem collision/reaction cell of any of embodiments 21-35; and a controller comprising an electronic processor and a memory, and configured to control the steps of generating the first RF electrical field superimposed on the first DC electrical field, generating the second RF electrical field superimposed on the second DC electrical field, generating the first DC potential barrier, and generating the second DC potential barrier according to any of embodiments 21-35.

37. The ICP-MS system of embodiment 36, comprising a mass analyzer communicating with the cell exit.

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the computing device 120 schematically depicted in FIG. 1. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), field-programmable gate arrays (FPGAs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the computing device 120 in FIG. 1), direct the electronic system to carry out the instructions. The computer program product may be selectively embodied in any non-transitory computer-readable storage medium for use by or in connection with an instruction execution system, apparatus, or device, such as an electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program may be electronically captured via, for instance, optical scanning of the paper or other medium, then compiled, interpreted, or otherwise processed in a suitable manner if necessary, and then stored in a computer memory or machine memory.

It will also be understood that terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A tandem collision/reaction cell, comprising:
    a housing comprising a cell entrance, a cell exit spaced from the cell entrance along a longitudinal axis of the collision/reaction cell, and a gas supply port communicating with an interior of the housing;
    a first ion guide positioned in the housing and comprising a first ion guide entrance and a first ion guide exit, the first ion guide configured to generate a first RF confining field effective to confine ions in a radial direction orthogonal to the longitudinal axis;
    a second ion guide positioned in the housing and comprising a second ion guide entrance and a second ion guide exit, the second ion guide configured to generate a second RF confining field effective to confine ions in a radial direction orthogonal to the longitudinal axis; and
    an intermediate electrode configured to generate an on-axis DC potential barrier in a vicinity of the first ion guide exit, wherein the on-axis DC potential barrier is effective to prevent at least some interfering ions from exiting the first ion guide and low enough to allow analyte ions of smaller cross-section than the interfering ions to exit the first ion guide.

2. The tandem collision/reaction cell of claim 1, wherein the on-axis DC potential barrier has a magnitude in a range from 0.1 V to 10 V.

3. The tandem collision/reaction cell of claim 1, wherein the first ion guide and the second ion guide are multipole ion guides.

4. The tandem collision/reaction cell of claim 3, wherein:
    the first ion guide comprises a plurality of elongated first ion guide electrodes positioned at a radial distance orthogonal to the longitudinal axis and circumferentially spaced from each other about the longitudinal axis, and defining the first ion guide entrance and the first ion guide exit; and
    the second ion guide comprises a plurality of elongated second ion guide electrodes positioned at a radial distance orthogonal to the longitudinal axis and circumferentially spaced from each other about the longitudinal axis, and defining the second ion guide entrance and the second ion guide exit, the second ion guide entrance being spaced from the first ion guide exit by an axial gap.

5. The tandem collision/reaction cell of claim 1, comprising a voltage source configured to apply a first RF potential superimposed on a first DC bias potential to electrodes of the first ion guide to generate the first RF confining field, apply a second RF potential superimposed on a second DC bias potential to electrodes of the second ion guide to generate the second RF confining field, and apply a third DC potential to the intermediate electrode to generate the on-axis DC potential barrier.

6. The tandem collision/reaction cell of claim 5, wherein the voltage source has a configuration selected from the group consisting of:
    the voltage source is configured to apply the first DC bias potential in a range from −50 V to −10 V;
    the voltage source is configured to apply the second DC bias potential in a range from −100 V to −20 V;
    the voltage source is configured to apply the third DC potential in a range from −50 V to +500 V; and
    a combination of two or more of the foregoing.

7. The tandem collision/reaction cell of claim 5, comprising an ion optics component positioned downstream from the second ion guide exit, wherein the voltage source is configured to apply a fourth DC potential to the ion optics component, and the fourth DC potential has a magnitude that produces an on-axis potential more positive than the second DC bias potential.

8. The tandem collision/reaction cell of claim 7, wherein the fourth DC potential is in a range from −90 V to 0 V.

9. The tandem collision/reaction cell of claim 1, wherein the intermediate electrode has a configuration selected from the group consisting of:
the intermediate electrode is a plate having an aperture surrounding the first ion guide at the first ion guide exit;
the intermediate electrode is a plate comprising an inside surface defining an aperture surrounding the first ion guide at the first ion guide exit, wherein the first ion guide comprises a plurality of first ion guide electrodes arranged in a multipole configuration, and the inside surface protrudes between the first ion guide electrodes;
the intermediate electrode is a plate having an aperture between the first ion guide exit and the second ion guide entrance;
the intermediate electrode is an ion guide positioned between the first ion guide exit and the second ion guide entrance, and is configured to generate a third RF confining field;
the intermediate electrode is a multipole ion guide positioned between the first ion guide exit and the second ion guide entrance, and is configured to generate a third RF confining field;
the intermediate electrode, the first ion guide, and the second ion guide are multipole ion guides, the intermediate electrode is positioned between the first ion guide exit and the second ion guide entrance, and the intermediate electrode has a shorter axial length than the first ion guide and the second ion guide; and
the intermediate electrode, the first ion guide, and the second ion guide are multipole ion guides, the intermediate electrode is positioned between the first ion guide exit and the second ion guide entrance, and the intermediate electrode has an axial length in a range of 10% to 60% of an axial length of the first ion guide and an axial length of the second ion guide.

10. The tandem collision/reaction cell of claim 1, comprising an ion optics component positioned downstream from the second ion guide exit and configured to generate a second DC potential barrier effective to prevent at least some interfering ions from passing through a mass analyzer downstream from the cell exit, and low enough to allow analyte ions to pass through the mass analyzer.

11. The tandem collision/reaction cell of claim 10, wherein the ion optics component has a position selected from the group consisting of:
the ion optics component is positioned at the cell exit;
the ion optics component is positioned outside of the housing;
the ion optics component is positioned between the cell exit and a mass analyzer;
the ion optics component is positioned at an entrance of a mass analyzer; and
the ion optics component is a mass analyzer.

12. An inductively coupled plasma-mass spectrometry (ICP-MS) system, comprising:
the tandem collision/reaction cell of claim 1; and
a mass analyzer communicating with the cell exit.

13. A method for operating a tandem collision/reaction cell in an inductively coupled plasma-mass spectrometry (ICP-MS) system, the method comprising:
flowing a collision/reaction gas into the tandem collision/reaction cell, the tandem collision/reaction cell comprising a cell entrance, a cell exit spaced from the cell entrance along a longitudinal axis of the tandem collision/reaction cell, a first ion guide between the cell entrance and a second ion guide, and the second ion guide between the first ion guide and the cell exit;
generating a first RF confining field in the first ion guide to confine ions in a radial direction orthogonal to the longitudinal axis;
generating a second RF confining field in the second ion guide to confine ions in a radial direction orthogonal to the longitudinal axis;
generating a first DC potential barrier in a vicinity of a first ion guide exit of the first ion guide;
generating a second DC potential barrier downstream from a second ion guide exit of the second ion guide;
transmitting analyte ions and interfering ions through the cell entrance and into the first ion guide, the analyte ions and the interfering ions having been produced from ionizing a sample under analysis, wherein the analyte ions and the interfering ions collide with the collision/reaction gas and lose kinetic energy, and the first DC potential barrier is high enough to prevent at least some of the interfering ions from exiting the first ion guide and low enough to allow the analyte ions to exit the first ion guide; and
transmitting the analyte ions from the first ion guide into the second ion guide, wherein the analyte ions and any interfering ions in the second ion guide collide with the collision/reaction gas and lose kinetic energy, and the second DC potential barrier is high enough to prevent at least some of the interfering ions from passing through a mass analyzer downstream from the cell exit, and low enough to allow the analyte ions to pass through the mass analyzer.

14. The method of claim 13, wherein the magnitudes of the first DC potential barrier and the second DC potential barrier are selected from the group consisting of:
the magnitude of the first DC potential barrier is in a range from 0.1 V to 10 V;
the magnitude of the second DC potential barrier is in a range from 0.1 V to 10 V; and
both of the foregoing.

15. A method for analyzing a sample, the method comprising:
producing analyte ions from the sample;
transmitting the analyte ions into the tandem collision/reaction cell of claim 14;
operating the tandem collision/reaction cell according to the method of claim 14; and
transmitting the analyte ions into a mass analyzer.

16. The method of claim 13, wherein the tandem collision/reaction cell comprises an intermediate electrode in a vicinity of the first ion guide exit, and generating the first DC potential barrier comprises applying a DC potential to the intermediate electrode.

17. The method of claim 13, comprising applying a first RF potential superimposed on a first DC bias potential to the first ion guide to generate the first RF confining field, and a second RF potential superimposed on a second DC bias potential to the second ion guide to generate the second RF confining field.

18. The method of claim 17, wherein the first DC bias potential and the second DC bias potential have magnitudes selected from the group consisting of:
- the first DC bias potential and the second DC bias potential have negative magnitudes;
- the first DC bias potential is in a range from −50 V to −10 V;
- the second DC bias potential is in a range from −100 V to −20 V; and
- the second DC bias potential is more negative than the first DC potential.

19. The method of claim 17, wherein the first DC bias potential and the second DC bias potential have a configuration selected from the group consisting of:
- at least one of the first DC bias potential or the second DC bias potential is constant along a length of the first ion guide or the second ion guide; and
- at least one of the first DC bias potential or the second DC bias potential is an axial DC potential gradient along a length of the first ion guide or the second ion guide.

20. The method of claim 13, comprising, before transmitting the analyte ions through the entrance and into the collision/reaction cell, performing an operation selected from the group consisting of:
- producing the analyte ions by exposing the sample to an inductively coupled plasma;
- producing the analyte ions by exposing the sample to an inductively coupled plasma produced by operating a plasma torch; and
- flowing the sample from a nebulizer or a spray chamber into a plasma torch, and producing the analyte ions by exposing the sample to an inductively coupled plasma produced by operating the plasma torch.

* * * * *